(12) United States Patent
Abe et al.

(10) Patent No.: US 11,185,308 B2
(45) Date of Patent: Nov. 30, 2021

(54) ULTRASOUND DIAGNOSIS APPARATUS, IMAGE PROCESSING APPARATUS, AND IMAGE PROCESSING METHOD

(71) Applicant: CANON MEDICAL SYSTEMS CORPORATION, Otawara (JP)

(72) Inventors: Yasuhiko Abe, Otawara (JP); Shogo Fukuda, Kawasaki (JP); Koji Ando, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 385 days.

(21) Appl. No.: 15/906,772

(22) Filed: Feb. 27, 2018

(65) Prior Publication Data
US 2018/0242950 A1   Aug. 30, 2018

(30) Foreign Application Priority Data
Feb. 28, 2017   (JP) .............................. JP2017-037413

(51) Int. Cl.
*A61B 8/14* (2006.01)
*A61B 8/00* (2006.01)
(Continued)

(52) U.S. Cl.
CPC ................ *A61B 8/466* (2013.01); *A61B 8/02* (2013.01); *A61B 8/12* (2013.01); *A61B 8/483* (2013.01);
(Continued)

(58) Field of Classification Search
CPC ......... A61B 5/0456; A61B 8/483; A61B 8/02; A61B 8/12; A61B 8/466; A61B 8/486;
(Continued)

(56) References Cited

U.S. PATENT DOCUMENTS

2009/0156935 A1\* 6/2009 Frisa ................... G01S 15/8925
600/447
2010/0249589 A1   9/2010 Lysyansky et al.
(Continued)

FOREIGN PATENT DOCUMENTS

JP   2008-515517   5/2008
JP   2010-051731 A   3/2010
(Continued)

OTHER PUBLICATIONS

Jackie S. McGhie, et al. "A Novel 13-Segment Standardized Model for Assessment of Right Ventricular Function Using Two-Dimensional iRotate Echocardiography", Echocardiography, 33:353-361, 2015.
(Continued)

*Primary Examiner* — Mark D Remaly
(74) *Attorney, Agent, or Firm* — Oblon, McClelland, Maier & Neustadt, L.L.P.

(57) ABSTRACT

In an ultrasound diagnosis apparatus according to an embodiment, processing circuitry obtains volume video data of a patient acquired by a transesophageal echocardiography probe. The processing circuitry sets, with the volume video data, a three-dimensional coordinate system that matches a display orientation of image data of the patient acquired by a body-surface ultrasound probe, on the basis of a positional relationship between the transesophageal echocardiography probe and the patient. The processing circuitry causes a display screen to display image data generated from the volume video data by using the set three-dimensional coordinate system. The processing circuitry receives, from an operator, a designation related to calculating movement information in a region of interest of the patient, the designation being received in an image displayed on the display screen. The processing circuitry calculates the movement
(Continued)

information by performing processing including a tracking process, while using the volume video data.

14 Claims, 11 Drawing Sheets

(51) Int. Cl.
| | |
|---|---|
| *A61B 8/02* | (2006.01) |
| *A61B 8/12* | (2006.01) |
| *A61B 8/08* | (2006.01) |
| *G06T 15/08* | (2011.01) |
| *G06T 7/246* | (2017.01) |
| *G06T 3/60* | (2006.01) |
| *G16H 30/40* | (2018.01) |
| *G16H 50/50* | (2018.01) |
| *G16H 50/20* | (2018.01) |
| *A61B 5/352* | (2021.01) |

(52) U.S. Cl.
CPC .............. *G06T 3/60* (2013.01); *G06T 7/248* (2017.01); *G06T 15/08* (2013.01); *G16H 30/40* (2018.01); *G16H 50/20* (2018.01); *G16H 50/50* (2018.01); *A61B 5/352* (2021.01); *A61B 8/486* (2013.01); *A61B 8/488* (2013.01); *G06T 2207/10016* (2013.01); *G06T 2207/10136* (2013.01); *G06T 2207/30048* (2013.01)

(58) Field of Classification Search
CPC ............... A61B 8/488; G06T 15/08; G06T 2207/10016; G06T 2207/10136; G06T 2207/30048; G06T 3/60; G06T 7/248; G16H 30/40; G16H 50/20; G16H 50/50
See application file for complete search history.

(56) References Cited

U.S. PATENT DOCUMENTS

| | | |
|---|---|---|
| 2011/0087094 A1 | 4/2011 | Ohuchi et al. |
| 2017/0116748 A1* | 4/2017 | Scutaru ............... G06K 9/6256 |

FOREIGN PATENT DOCUMENTS

| | | |
|---|---|---|
| JP | 2010-227568 | 10/2010 |
| JP | 2011-78625 | 4/2011 |
| JP | 2012-217780 | 11/2012 |
| JP | 2012-245221 A | 12/2012 |
| JP | 2013-000414 A | 1/2013 |

OTHER PUBLICATIONS

Japanese Office Action dated Oct. 20, 2020, issued in Japanese Patent Application No. 2017-037413.

Japanese Office Action dated Jan. 26, 2021, issued in Japanese Patent Application No. 2017-037413 (with English translation).

* cited by examiner

FIG.2A
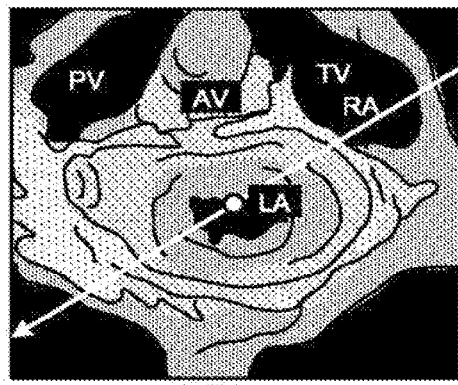
SURGEON'S VIEW
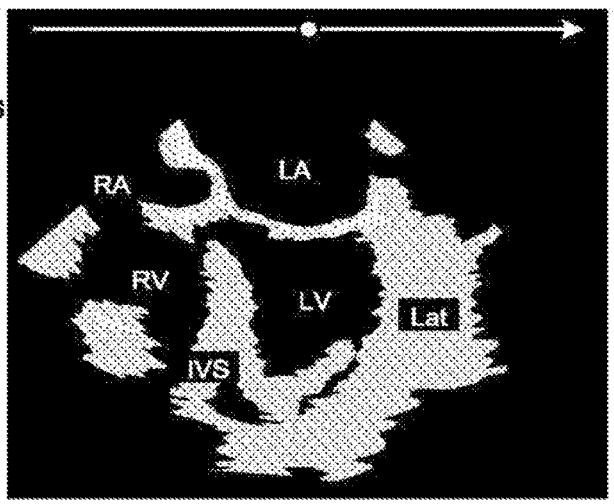
MPR IMAGE (0 DEGREES)
FIG.2B
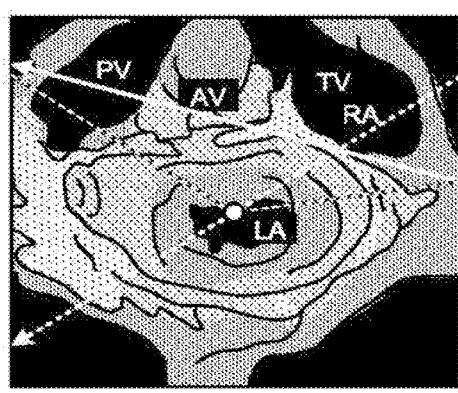
SURGEON'S VIEW
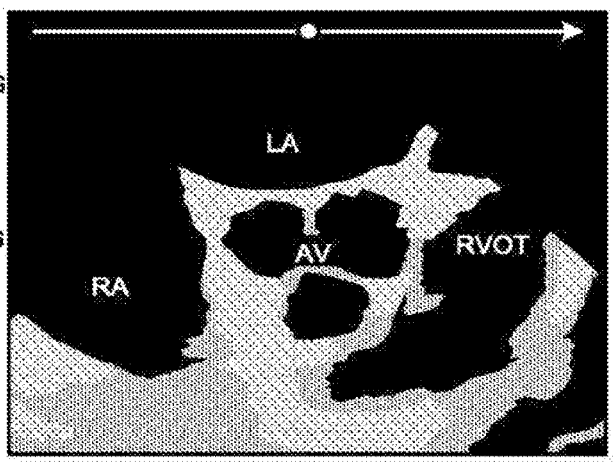
MPR IMAGE (45 DEGREES)
FIG.2C
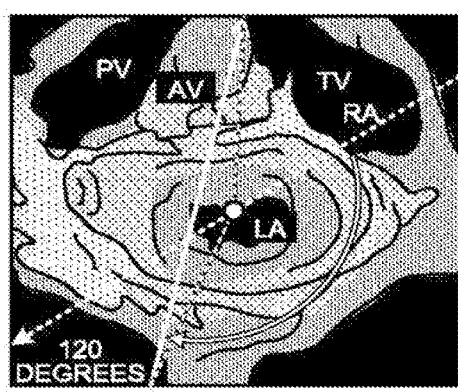
SURGEON'S VIEW
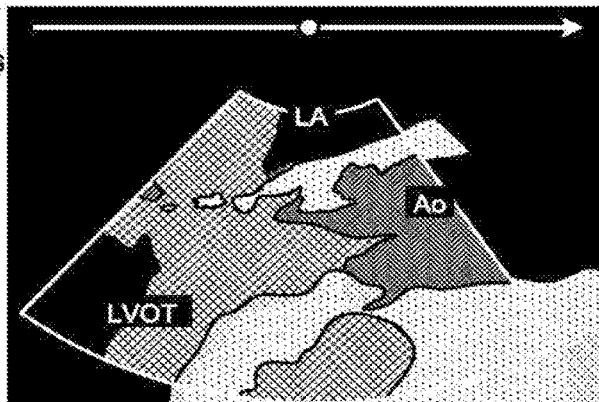
MPR IMAGE (120 DEGREES)

ULTRASOUND DIAGNOSIS APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2017-037413, filed on Feb. 28, 2017; the entire contents of which are incorporated herein by reference.

FIELD

Embodiments described herein relate generally to an ultrasound diagnosis apparatus, an image processing apparatus, and an image processing method.

BACKGROUND

Conventionally, transesophageal echocardiography (TEE) probes have been used in ultrasound diagnosis apparatuses. Such TEE probes are ultrasound probes used for imaging the heart or the like with ultrasound waves, as being orally inserted into an upper gastrointestinal tract such as the esophagus or the stomach.

Generally speaking, ultrasound images are generated according to the usual practice where the shallower side in terms of the depth direction is rendered on the upper side of a display image. For this reason, ultrasound images of the heart or the like imaged by using a TEE probe are substantially upside down (i.e., the up-and-down direction is inverted), compared to ultrasound images taken by using a body-surface probe.

BRIEF DESCRIPTION OF THE DRAWINGS

FIGS. 2A to 2C are drawings illustrating examples of Multi Planar Reconstruction (MPR) images generated from volume data acquired by a TEE probe;

DETAILED DESCRIPTION

It is an object of the present disclosure to provide an ultrasound diagnosis apparatus, an image processing apparatus, and an image processing computer program that are capable of making simple and convenient three-dimensional processing performed on image data acquired by a transesophageal echocardiography probe.

An ultrasound diagnosis apparatus according to an embodiment includes processing circuitry. The processing circuitry is configured to obtain volume video data of a patient acquired by a transesophageal echocardiography probe. The processing circuitry is configured to set, with the volume video data, a three-dimensional coordinate system that matches a display orientation of image data of the patient acquired by a body-surface ultrasound probe, on the basis of a positional relationship between the transesophageal echocardiography probe and the patient. The processing circuitry is configured to cause a display screen to display image data generated from the volume video data by using the set three-dimensional coordinate system. The processing circuitry is configured to receive, from an operator, a designation related to calculating movement information in a region of interest of the patient, the designation being received in an image displayed on the display screen. The processing circuitry is configured to calculate the movement information by performing processing including a tracking process, while using the volume video data.

Exemplary embodiments of an ultrasound diagnosis, an image processing apparatus, and an image processing method will be explained below, with reference to the accompanying drawings. The embodiments described below are not limited to the explanations presented below. It is possible to combine each of the embodiments described below with another embodiment or a conventional technique as long as no conflict occurs in the contents of the processing.

First Embodiment

Figure 1:
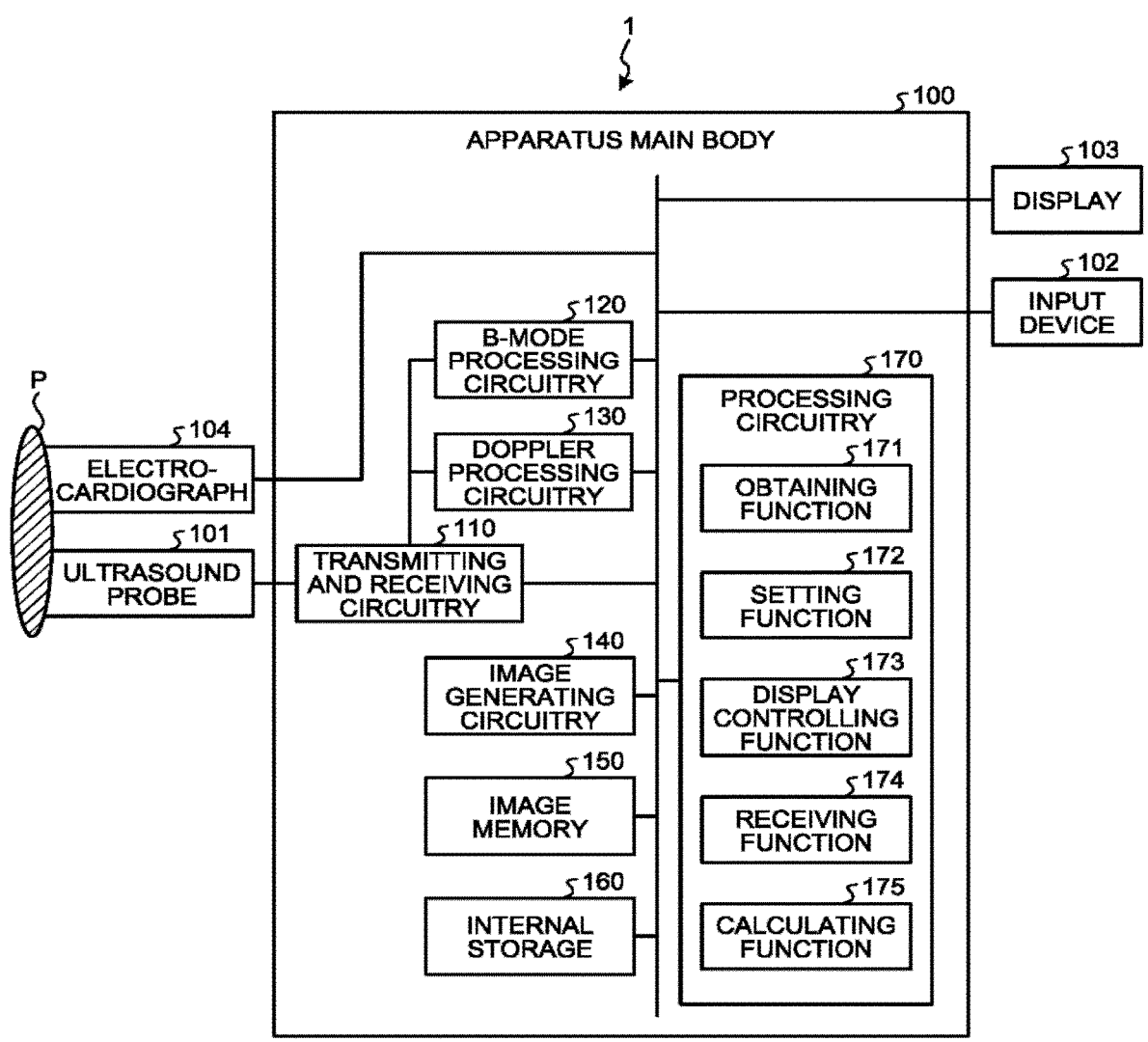
FIG. 1 is a block diagram illustrating an exemplary configuration of an ultrasound diagnosis apparatus according to a first embodiment.

At first, a configuration of an ultrasound diagnosis apparatus according to a first embodiment will be explained. FIG. 1 is a block diagram illustrating an exemplary configuration of an ultrasound diagnosis apparatus 1 according to the first embodiment. As illustrated in FIG. 1, the ultrasound diagnosis apparatus 1 according to the first embodiment includes an apparatus main body 100, an ultrasound probe 101, an input device 102, a display 103, and an electrocardiograph 104. The ultrasound probe 101, the input device 102, the display 103, and the electrocardiograph 104 are connected to the apparatus main body 100 so as to be able to communicate therewith.

The ultrasound probe 101 includes a plurality of transducer elements. Each of the plurality of transducer elements is configured to generate an ultrasound wave on the basis of a drive signal supplied thereto from transmitting and receiving circuitry 110 included in the apparatus main body 100.

Further, the ultrasound probe 101 is configured to receive reflected waves coming from an examined subject (hereinafter "patient") P and to convert the received reflected waves into an electrical signal. The ultrasound probe 101 includes matching layers provided for the transducer elements, as well as a backing member or the like that prevents the ultrasound waves from propagating rearward from the transducer elements. The ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected-wave signal by each of the plurality of transducer elements included in the ultrasound probe 101. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

The ultrasound probe 101 according to the first embodiment is, for example, a Transesophageal Echocardiography (TEE) probe capable of acquiring volume data. The TEE probe serves as the ultrasound probe 101 used for imaging the heart or the like with ultrasound waves, as being orally inserted into an upper gastrointestinal tract such as the esophagus or the stomach. In one example, the ultrasound probe 101 may be a multi-plane TEE probe including a one-dimensional array in which the plurality of transducer elements are arranged in a row. Such a multi-plane TEE probe is configured to acquire volume data, by mechanically rotating the surface of the transducer elements that scans a cross-sectional plane (a plane surface). In another example, the ultrasound probe 101 may be a three-dimensional (3D) TEE probe including a two-dimensional array in which the plurality of transducer elements are arranged in a grid formation. Such a 3D-TEE probe is capable of arbitrarily setting a direction of a cross-sectional plane by performing an electronic scan. For example, a 3D-TEE probe is configured to acquire volume data by deflecting a cross-sectional plane while performing an electronic scan.

The input device 102 includes a mouse, a keyboard, a button, a panel switch, a touch command screen, a foot switch, a trackball, a joystick, and/or the like. The input device 102 is configured to receive various types of setting requests from an operator of the ultrasound diagnosis apparatus 1 and to transfer the received various types of setting requests to the apparatus main body 100.

The display 103 is configured to display a Graphical User Interface (GUI) used by the operator of the ultrasound diagnosis apparatus 1 to input the various types of setting requests through the input device 102 and to display ultrasound image data generated by the apparatus main body 100 or the like. Further, the display 103 is configured to display various types of messages to inform the operator of processing statuses of the apparatus main body 100. Further, the display 103 includes a speaker and is also capable of outputting audio. For example, the speaker included in the display 103 is configured to output a predetermined sound such as a beep sound, to inform the operator of a processing status of the apparatus main body 100.

The electrocardiograph 104 is configured to acquire an electrocardiogram (ECG) of the patient P, as a biological signal of the patient P who is two-dimensionally scanned. The electrocardiograph 104 transmits the acquired electrocardiogram to the apparatus main body 100. In the present embodiment, an example will be explained in which the electrocardiograph 104 is used as a means for acquiring information about cardiac temporal phases of the heart of the patient P; however, possible embodiments are not limited to this example. For instance, the ultrasound diagnosis apparatus 1 may acquire the information about the cardiac temporal phases of the heart of the patient P, by acquiring time related to the first heart sound (S1) or the second heart sound (S2) in a phonocardiogram or a Mitral Valve Closure (MVC) time or an Aortic Valve Closure (AVC) time obtained by measuring an incoming blood flow to, or an ejected blood flow from, the left ventricle through a spectrum Doppler procedure.

The apparatus main body 100 is an apparatus configured to generate ultrasound image data on the basis of the reflected-wave signals received by the ultrasound probe 101. The apparatus main body 100 illustrated in FIG. 1 is an apparatus capable of generating two-dimensional ultrasound image data on the basis of two-dimensional reflected-wave data received by the ultrasound probe 101. Further, the apparatus main body 100 is an apparatus capable of generating three-dimensional ultrasound image data on the basis of three-dimensional reflected-wave data received by the ultrasound probe 101.

As illustrated in FIG. 1, the apparatus main body 100 includes the transmitting and receiving circuitry 110, B-mode processing circuitry 120, Doppler processing circuitry 130, image generating circuitry 140, an image memory 150, internal storage 160, and processing circuitry 170. The transmitting and receiving circuitry 110, the B-mode processing circuitry 120, the Doppler processing circuitry 130, the image generating circuitry 140, the image memory 150, the internal storage 160, and the processing circuitry 170 are connected together so as to be able to communicate with one another.

The transmitting and receiving circuitry 110 includes a pulse generator, a transmission delay unit, a pulser, and the like and is configured to supply the drive signal to the ultrasound probe 101. The pulse generator is configured to repeatedly generate a rate pulse used for forming a transmission ultrasound wave, at a predetermined rate frequency. Further, the transmission delay unit is configured to apply a delay period that is required to converge the ultrasound wave generated by the ultrasound probe 101 into the form of a beam and to determine transmission directionality and that corresponds to each of the transducer elements, to each of the rate pulses generated by the pulse generator. Further, the pulser is configured to apply the drive signal (a drive pulse) to the ultrasound probe 101 with timing based on the rate pulses. In other words, by varying the delay periods applied to the rate pulses, the transmission delay unit arbitrarily adjusts the transmission directions of the ultrasound waves transmitted from the surface of the transducer elements.

The transmitting and receiving circuitry 110 has a function to be able to instantly change the transmission frequency, the transmission drive voltage, and the like, for the purpose of executing a predetermined scanning sequence on the basis of an instruction from the processing circuitry 170 (explained later). In particular, the configuration to change the transmission drive voltage is realized by using a linear-amplifier-type transmission circuit of which the value can be instantly switched or by using a mechanism configured to electrically switch between a plurality of power source units.

Further, the transmitting and receiving circuitry 110 includes a pre-amplifier, an Analog/Digital (A/D) converter, a reception delay unit, an adder, and the like. The transmitting and receiving circuitry 110 is configured to generate the reflected-wave data by performing various types of processes on the reflected-wave signals received by the ultrasound probe 101. The pre-amplifier is configured to amplify the reflected-wave signal for each of the channels. The A/D converter is configured to apply an A/D conversion to the amplified reflected-wave signals. The reception delay unit is configured to apply a delay period required to determine reception directionality. The adder is configured to generate the reflected-wave data by performing an adding process on the reflected-wave signals processed by the reception delay unit. As a result of the adding process performed by the adder, reflected components from the direction corresponding to the reception directionality of the reflected-wave signals are emphasized, so that a comprehensive beam for transmitting and receiving the ultrasound wave is formed on the basis of the reception directionality and the transmission directionality.

As for the mode of output signals from the transmitting and receiving circuitry 110, it is possible to select from among various modes such as a mode in which the output signal is a signal called a Radio Frequency (RF) signal that includes phase information or a mode in which the output signal is represented with amplitude information resulting from an envelope detecting process.

The B-mode processing circuitry 120 is configured to generate data (B-mode data) in which the signal intensity is expressed as a level of brightness, by receiving the reflected-wave data from the transmitting and receiving circuitry 110 and performing a logarithmic amplifying process, an envelope detecting process, or the like thereon.

The Doppler processing circuitry 130 is configured to generate data (Doppler data) obtained by performing a frequency analysis on the reflected-wave data received from the transmitting and receiving circuitry 110 to acquire velocity information, extracting blood flows, tissues, and contrast-agent echo components subject to the Doppler effect, and extracting moving member information such as a velocity value, a variance value, a power value, and the like from multiple points.

The B-mode processing circuitry 120 and the Doppler processing circuitry 130 illustrated in FIG. 1 are each capable of processing both two-dimensional reflected-wave data and three-dimensional reflected-wave data. In other words, the B-mode processing circuitry 120 is configured to generate two-dimensional B-mode data from the two-dimensional reflected-wave data and to generate three-dimensional B-mode data from the three-dimensional reflected-wave data. Further, the Doppler processing circuitry 130 is configured to generate two-dimensional Doppler data from the two-dimensional reflected-wave data and to generate three-dimensional Doppler data from the three-dimensional reflected-wave data.

The image generating circuitry 140 is configured to generate ultrasound image data from the data generated by the B-mode processing circuitry 120 and the Doppler processing circuitry 130. In other words, from the two-dimensional B-mode data generated by the B-mode processing circuitry 120, the image generating circuitry 140 is configured to generate two-dimensional B-mode image data in which intensities of the reflected waves are expressed with levels of brightness. Further, from the two-dimensional Doppler data generated by the Doppler processing circuitry 130, the image generating circuitry 140 is configured to generate two-dimensional Doppler image data expressing the moving member information. The two-dimensional Doppler image data may be a velocity image, a dispersion image, a power image, or an image combining any of these images. Further, the image generating circuitry 140 is also capable of generating M-mode image data from time-series data of B-mode data on one scan line generated by the B-mode processing circuitry 120. Further, the image generating circuitry 140 is also capable of generating a Doppler waveform obtained by plotting velocity information of a blood flow or a tissue in a time-series, from the Doppler data generated by the Doppler processing circuitry 130.

In this situation, generally speaking, the image generating circuitry 140 is configured to generate display-purpose ultrasound image data by converting (performing a scan convert process on) a scanning line signal sequence from an ultrasound scan into a scanning line signal sequence in a video format used by, for example, television. More specifically, the image generating circuitry 140 is configured to generate the display-purpose ultrasound image data by performing a coordinate transformation process corresponding to the ultrasound scanning mode used by the ultrasound probe 101. Further, as various types of image processing processes other than the scan convert process, the image generating circuitry 140 performs, for example, an image processing process (called a smoothing process) to re-generate an average brightness value image by using a plurality of image frames resulting from the scan convert process and an image processing process (called an edge enhancement process) performed by using a differential filter within an image. Further, the image generating circuitry 140 combines ultrasound image data with text information of various parameters, scale graduations, body marks, and/or the like.

In other words, the B-mode data and the Doppler data are each ultrasound image data before the scan convert process is performed. In contrast, the data generated by the image generating circuitry 140 is the display-purpose ultrasound image data after the scan convert process is performed. The B-mode data and the Doppler data may each be referred to as raw data. The image generating circuitry 140 generates "two-dimensional B-mode image data or two-dimensional Doppler image data" that is display-purpose two-dimensional ultrasound image data, from "two-dimensional B-mode data or two-dimensional Doppler data" that is two-dimensional ultrasound image data before the scan convert process is performed.

The image memory 150 is a memory storing therein the display-purpose image data generated by the image generating circuitry 140. Further, the image memory 150 is also capable of storing therein the data generated by the B-mode processing circuitry 120 and the Doppler processing circuitry 130. The B-mode data and the Doppler data stored in the image memory 150 may be, for example, invoked by the operator after a diagnosis procedure and may serve as display-purpose ultrasound image data after being routed through the image generating circuitry 140.

The image generating circuitry 140 is configured to store, into the image memory 150, the ultrasound image data and a time at which an ultrasound scan was performed to generate the ultrasound image data, so as to be kept in correspondence with an electrocardiogram waveform transmitted thereto from the electrocardiograph 104. By referring to the data stored in the image memory 150, the processing circuitry 170 (explained later) is able to obtain cardiac temporal phases exhibited during the ultrasound scan performed to generate the ultrasound image data.

The internal storage 160 is configured to store therein a control computer program (hereinafter "control program") used for performing an ultrasound transmission/reception, image processing processes, and displaying processes, as well as various types of data such as diagnosis information (e.g., patients' IDs, observations of medical doctors, etc.), diagnosis protocols, various types of body marks, and the like. Further, the internal storage 160 may also be used for storing therein any of the image data stored in the image memory 150, as necessary. Further, it is also possible to transfer any of the data stored in the internal storage 160 to an external apparatus via an interface (not illustrated). The external apparatus may be, for example, a Personal Computer (PC) used by a medical doctor who performs an image diagnosis process, a storage medium such as a Compact Disk (CD) or a Digital Versatile Disk (DVD), a printer, or the like.

The processing circuitry 170 is configured to control the overall processing of the ultrasound diagnosis apparatus 1. More specifically, the processing circuitry 170 is configured to control processes performed by the transmitting and receiving circuitry 110, the B-mode processing circuitry 120, the Doppler processing circuitry 130, and the image generating circuitry 140, on the basis of the various types of setting requests input by the operator via the input device 102 and various types of control programs and various types of data read from the internal storage 160. Further, the processing circuitry 170 exercises control so that the display 103 displays the display-purpose ultrasound image data stored in the image memory 150 and the internal storage 160.

Further, the processing circuitry 170 executes an obtaining function 171, a setting function 172, a display controlling function 173, a receiving function 174, and a calculating function 175. In this situation, the obtaining function 171 is an example of an obtaining unit. The setting function 172 is an example of a setting unit. The display controlling function 173 is an example of a display controlling unit. The receiving function 174 is an example of a receiving unit. The calculating function 175 is an example of a calculating unit. Contents of the processes performed by the obtaining function 171, the setting function 172, the display controlling function 173, the receiving function 174, and the calculating function 175 executed by the processing circuitry 170 will be explained later.

In this situation, for example, the processing functions executed by the obtaining function 171, the setting function 172, the display controlling function 173, the receiving function 174, and the calculating function 175, which are constituent elements of the processing circuitry 170 illustrated in FIG. 1, are recorded in the internal storage 160 in the form of computer-executable programs. The processing circuitry 170 is a processor configured to realize the functions corresponding to the programs by reading and executing the programs from the internal storage 160. In other words, the processing circuitry 170 that has read the programs has the functions illustrated within the processing circuitry 170 in FIG. 1.

In the present embodiment, an example is explained in which the single processing circuit (i.e., the processing circuitry 170) realizes the processing functions explained below; however, another arrangement is also acceptable in which processing circuitry is structured by combining together a plurality of independent processors so that the functions are realized as a result of each of the processors executing a corresponding one of the programs.

The term "processor" used in the above explanation denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors each realize the function thereof by reading and executing a corresponding one of the programs stored in the internal storage 160. It is also acceptable to directly incorporate the programs into the circuits of the processors, instead of storing the programs in the internal storage 160. In that situation, each of the processors realizes the function thereof by reading and executing the program incorporated in the circuit thereof. Further, as for the processors according to the present embodiment, each of the processors may be structured as a single circuit. Alternatively, it is also acceptable to realize the functions thereof by structuring a single processor by combining together a plurality of independent circuits. Further, it is also acceptable to integrate two or more of the constituent elements illustrated in each of the drawings into one processor so as to realize the functions thereof.

In this situation, from an application that performs three-dimensional processing while using volume video data such as a 3D Wall Motion Tracking (WMT) process that uses a three-dimensional speckle tracking technique, an analysis result is output to indicate, for example, myocardial strain related to the left ventricle (LV) or the right ventricle (RV) of the heart. In this situation, when volume video data of the heart is acquired by using a body-surface probe realized with an ultrasound probe configured to perform an ultrasound scan while being kept in contact with the body surface of the patient, a commonly-used method is to acquire the data by implementing a cardiac apex approach method, which is able to cover the region of the left ventricle or the right ventricle. When an arbitrary cross-sectional plane rendered in the volume video data is displayed as a Multi Planar Reconstruction (MPR) image, a commonly-used display scheme is a scheme by which a cardiac apex part positioned closer to the body surface is displayed on the upper side of the display image, whereas the atrium side positioned away from the body surface is displayed on the lower side of the display image. This scheme is used because, according to a common practice of a pulse echo method, the depth direction of an acquired data space is assigned to the up-and-down direction of an image, so that the side positioned closer to the surface of the transducer elements and having shorter reception periods is displayed on the upper side of a display image. Accordingly, for example, the application that performs the 3D WMT process by using volume video data acquired by a body-surface probe is designed on the basis of the display scheme by which a cardiac apex part is displayed on the upper side of a display image, whereas the atrium side is displayed on the lower side of the display image and therefore has operability unique to this display scheme.

Further, in recent years, it is also possible to acquire volume video data of the heart by using a TEE probe. With an example being the technique described in Patent Literature 2 (Japanese Patent Publication No. 2012-217780), techniques are known by which a cardiac valve is imaged in three-dimensional segmentation (a region extracting process) and by which the position of an extracted valve region is tracked either two-dimensionally or three-dimensionally. In this regard, when volume video data of the heart is acquired by using a TEE probe, the heart is approached from the atrium side, which is closer to the esophagus, on the contrary to the situation with a body-surface probe. When the volume video data acquired in this manner is displayed as an MPR image, according to a commonly-used display scheme, the atrium side positioned closer to the esophagus is displayed on the upper side of the display image, whereas the cardiac apex side positioned away from the esophagus is displayed on the lower side of the display image. As explained herein, the approach to the heart is made in the opposite direction with respect to the central axis of the heart extending from the cardiac apex to the atrium. Accordingly, between the data space of the volume video data acquired by using the body-surface probe and the data space of the volume video data acquired by using the TEE probe, the up-and-down directions, which correspond to the depth directions, are in a relationship of being inverted (opposite) from each other. Consequently, the MPR image displayed by using the volume video data acquired by using the TEE probe is displayed while the up-and-down direction is inverted (i.e., upside down) with respect to the heart, compared to the image acquired by using the body-surface probe.

MPR images generated from volume data acquired by the TEE probe will be explained, with reference to FIGS. 2A, 2B, and 2C. FIGS. 2A, 2B, and 2C are drawings illustrating examples of MPR images generated from volume data acquired by a TEE probe. The right section of FIG. 2A illustrates an MPR image in a situation where the rotation angle of the TEE probe is 0 degrees. The right section of FIG. 2B illustrates an MPR image in a situation where the rotation angle of the TEE probe is 45 degrees. The right section of FIG. 2C illustrates an MPR image in a situation where the rotation angle of the TEE probe is 120 degrees. The left section of each of FIGS. 2A, 2B, and 2C illustrates an image of the heart viewed from the left atrium side (i.e., a so-called surgeon's view rendered with a viewpoint of a surgeon). The cross-sectional position corresponding to the respective rotation angle is indicated in each of the images. The rotation angle of the TEE probe denotes the angle of the scanned cross-sectional plane with respect to the TEE probe. The direction orthogonal to the extending direction of the TEE probe is defined as 0 degrees.

As indicated in the right section of FIG. 2A, the MPR image corresponding to the rotation angle of 0 degrees renders the left ventricle (LV), the right ventricle (RV), the left atrium (LA), and the right atrium (RA) and looks similar to an upside-down A4C image. Further, in the MPR image corresponding to the rotation angle of 0 degrees, the interventricular septal wall (IVS) is rendered on the left side of the left ventricle, while the left ventricular lateral wall (Lat) is rendered on the right side of the left ventricle. Further, as indicated in the right section of FIG. 2B, the MPR image corresponding to the rotation angle of 45 degrees renders the right atrium (RA) and the right ventricular outflow tract (RVOT) and looks similar to a right-ventricular coronal view at the level of the aortic valve. Further, as illustrated in FIG. 2C, the MPR image corresponding to the rotation angle of 120 degrees renders the left atrium (LA) and the left ventricular outflow tract (LVOT) and looks similar to an upside-down A3C image. As explained herein, in the MPR images derived from the TEE probe, the up-and-down direction in each display image is inverted (upside down), compared to the MPR images (see, for example, FIG. 9 explained later) derived from a body-surface probe.

Incidentally, it is generally known that, when the right ventricle is observed by using a body-surface probe, some parts of the right ventricle are easy to see and other parts are difficult to see and that, in particular, the right ventricular outflow tract (RVOT) is difficult to see. In an example presented in Non-Patent Literature 1 (J S McGhie et al, "A Novel 13-Segment Standardized Model for Assessment of Right Ventricular Function Using Two-Dimensional iRotate Echocardiography," Echocardiography 33 (3), 353-361 (2015)) in which visibility was studied by rotating a scanned surface while using a two-dimensional array ultrasound probe capable of acquiring volume video data, the visibility ratios of the right ventricular outflow tract were 23% for healthy subjects and 75% for diseased subjects. In particular, it was reported that the rendering was found to be difficult with the healthy subjects. Accordingly, there is a problem where, when a 3D WMT process is applied to the right ventricle while using a body-surface probe, the quality of the analysis on the region of the right ventricular outflow tract, in particular, may be degraded.

When an apex approach is made from the body surface, because the scanned angle is larger on the right ventricular outflow tract side and because the location is positioned close to the ribs, the passage of ultrasound waves is limited with respect to the opening of the ultrasound probe. In addition, because the sternum and the right lung (which contains a lot of air and therefore does not pass ultrasound waves) that do not pass ultrasound waves are positioned in the surroundings nearby, the signal intensities of the ultrasound waves are consequently attenuated, and it is difficult for transmission and reception beams to be formed. This explains one of the reasons why it is difficult for the region of the right ventricular outflow tract to be rendered when a body-surface probe is used.

In this situation, when an approach is made by using a TEE probe, because it is possible to let the ultrasound waves pass from the esophagus side where there is no obstruction caused by the ribs, it is possible to form transmission and reception beams while maintaining the signal intensities even in the surroundings of the right ventricular outflow tract. It is therefore easier to render the region of the right ventricular outflow tract (see FIG. 2B). Accordingly, when a 3D WMT process is applied to the right ventricle, it is possible to improve the quality of the analysis made on the region of the right ventricular outflow tract, by using volume video data acquired by a TEE probe.

However, as explained above, between the TEE probe and the body-surface probe, the up-and-down direction in the display image is inverted (upside down), as compared with each other. For this reason, when volume video data acquired by a TEE probe is applied to a conventional application designed for analyzing volume video data acquired by a body-surface probe, the user would find it difficult to use because of the difference in operability. In particular, the more accustomed the operator is to the operability of the conventional application, the more strongly the operator feels the difference in the operability during the use.

To solve the problem described above, it is an object of the ultrasound diagnosis apparatus 1 according to the present embodiment to make simple and convenient the three-dimensional processing performed on the image data acquired by the transesophageal echocardiography probe.

Accordingly, the ultrasound diagnosis apparatus 1 according to the present embodiment is configured to invert the direction corresponding to the up-and-down direction of a display screen, in a three-dimensional coordinate system of the volume data acquired by the ultrasound probe 101 realized with a TEE probe, before applying the volume data to a conventional application. In this situation, it is possible to avoid the problem of the operability difference described above, by displaying an MPR image in the same orientation as the orientation of an image used when a 3D WMT analysis is performed by using a body-surface probe. Further, to realize the display in this manner, the ultrasound diagnosis apparatus 1 is configured to apply an appropriate coordinate transformation to the volume data acquired by the TEE probe, so as to match the coordinate system of the volume data acquired by the body-surface probe.

In relation to this, a technique is known by which, regardless of whether the probe is a body-surface probe or a TEE probe, acquired volume data is displayed after inverting the up-and-down direction (or the left-and-right direction) of a display screen. According to the technique disclosed in Patent Literature 3 (Japanese Patent Publication No. 2008-515517), an operator issues an instruction, when necessary, to invert the up-and-down direction (or the left-and-right direction), by performing an operation such as pressing a dedicated button, or the like. However, Patent Literature 3 does not disclose any specific requirements for arranging the three-dimensional orientation of volume data acquired by a TEE probe to match the three-dimensional orientation of volume data acquired by a body-surface probe.

Further, another technique is also known by which a two-dimensional speckle tracking (2DT) application is applied to a plurality of MPR cross-sectional planes by using volume data acquired by a TEE probe. However, the technique disclosed in Patent Literature 1 (Japanese Patent Publication No. 2010-227568) is limited to use with 2DT. Patent Literature 1 does not disclose any requirements for applying the technique to three-dimensional speckle tracking (3DT). Also, Patent Literature 1 does not disclose any requirements for inverting a display upside down in the situation where a TEE probe is used.

In view of these circumstances, the ultrasound diagnosis apparatus 1 according to the present embodiment is configured to apply an appropriate coordinate transformation to a data space of volume data acquired by a TEE probe so as to match the coordinate system of a data space of volume data acquired by a body-surface probe. In other words, the ultrasound diagnosis apparatus 1 according to the present embodiment is configured to set, with the volume video data, a three-dimensional coordinate system that matches the display orientation of the image data of the patient P acquired by a body-surface probe, on the basis of a positional relationship between the TEE probe and the patient P. With this arrangement, the ultrasound diagnosis apparatus 1 according to the present embodiment is able to make simple and convenient the three-dimensional processing performed on the image data acquired by the TEE probe.

In this situation, when the up-and-down direction is inverted in the data space of the volume data, there are two possible mirror-image inverted coordinate systems that each have the possibility of fitting the purpose. It is therefore necessary to appropriately select one of the two possible coordinate systems that matches the current setting state. This selection will automatically be made on the basis of a positional relationship between the TEE probe and the heart rendered in the acquired volume data.

Figure 3:
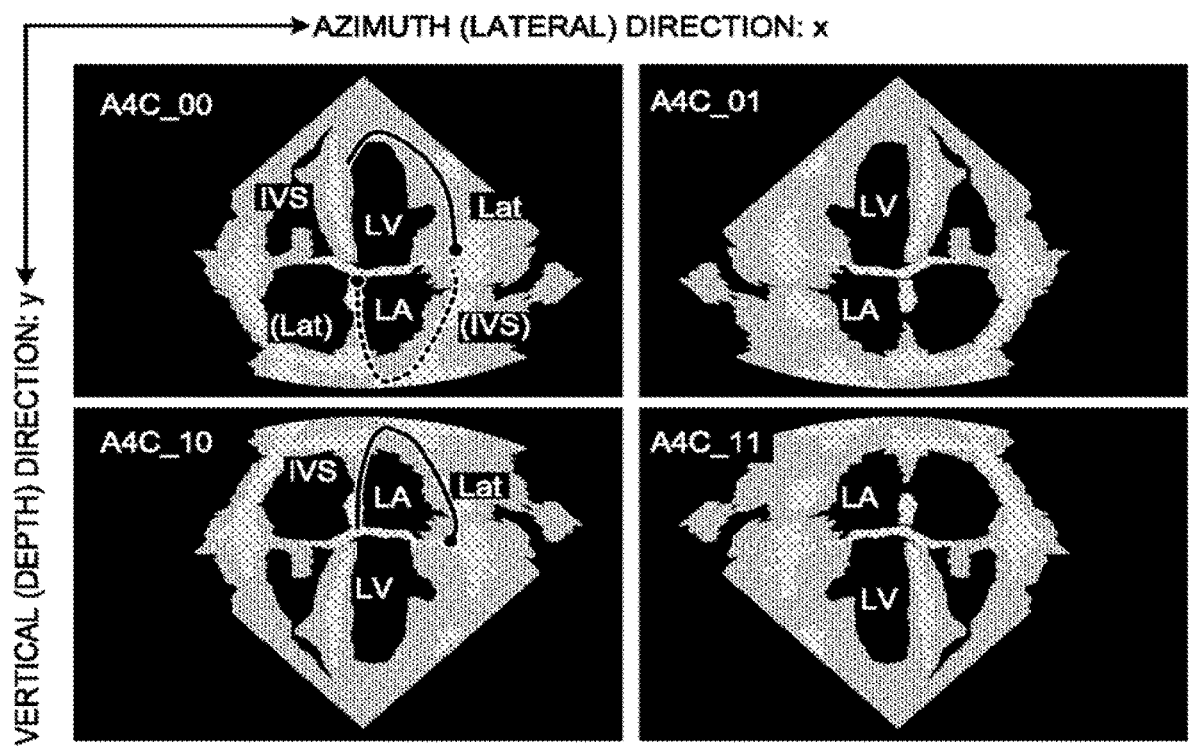
FIG. 3 is a drawing for explaining inverted coordinate systems in a situation where a data space is two-dimensional.

This function will be explained with reference to FIG. 3, while using a simplified example of two-dimensional images of which the data space is two-dimensional. FIG. 3 is a drawing for explaining inverted coordinate systems in the situation where the data space is two-dimensional. FIG. 3 illustrates an apical four-chamber (A4C) image derived from a body-surface probe. In FIG. 3, the text "A4C_yx (where y and x are each either "1" or "0")" in the top left corner of each of the four cross-sectional images indicates whether or not an inversion has been arranged in each of the directions. More specifically, when "y=0", it means that the y-direction has not been inverted. Conversely, when "y=1", it means that the y-direction has been inverted. Further, when "x=0", it means that the x-direction has not been inverted. Conversely, when "x=1", it means that the x-direction has been inverted. In other words, the text "A4C_00" denotes an A4C image in which neither the y-direction nor the x-direction has been inverted. The text "A4C_10" denotes an A4C image in which the y-direction has been inverted, but the x-direction has not been inverted. The text "A4C_01" denotes an A4C image in which the y-direction has not been inverted, but the x-direction has been inverted. Further, the text "A4C_11" denotes an A4C image in which the y-direction and the x-direction have been inverted.

The image "A4C_00" illustrated in the upper left section of FIG. 3 is based on the most commonly-used display scheme among those used with A4C images derived from a body-surface probe. As for the positional relationship with respect to the left ventricle (LV) in the x-direction (the azimuth direction), the right side corresponds to the lateral wall side, whereas the left side corresponds to the interventricular septum (IVS) side. In contrast, the image "A4C_01" illustrated in the upper right section of FIG. 3 is based on a display scheme used by Mayo Clinic in the U.S.A. among others, and although the y-direction (the depth direction) has not been inverted, the x-direction (the azimuth direction) has been inverted. For two-dimensional images, there are two possible display schemes, such as one view from the front side of the drawing page (hereinafter, "page-front side") and the other view from the rear side of the drawing page (hereinafter, "page-rear side"). For example, when "A4C_00" corresponds to the page-front side view, "A4C_01" corresponds to the page-rear side view. These two images are in a relationship of mirror-image inverted coordinate systems. Besides A4C images, examples of typical reference cross-sectional planes used in ultrasound diagnosis processes on the heart performed with a body-surface probe include A2C images, A3C images, P-LAX images, and SAX images. Except for A4C images for which the commonly-used display scheme and the Mayo Clinic display scheme are both used, it is customarily determined whether the page-front side view or the page-rear side view is used in the coordinate system, uniquely for each of the cross-sectional planes. For example, in A2C images, the right side corresponds to the anterior wall, whereas the left side corresponds to the inferior wall. In A3C images, the right side corresponds to the anteroseptum, whereas the left side corresponds to the posterior wall. These are based on customary rules that are similar to the rules applied to slice tomographic images (axial images) in Computed Tomography (CT) and Magnetic Resonance Imaging (MRI) procedures where misunderstanding for the left and the right direction is avoided by using a universal definition of directions by which the left and the right directions are determined from the feet side.

Next, an example will be explained in which, while using the "A4C_00" image, the endocardium of the left ventricle (LV) is traced as a region of interest in a 2DT application. As indicated with the solid line in the upper left section of FIG. 3, an example will be explained in which an application is configured to perform a tracing operation counterclockwise from the annulus of the heart valve positioned on the lateral (Lat) side to the annulus of the heart valve positioned on the interventricular septum (IVS) side, via a cardiac apex part. In that situation, according to the definition of directions in the "A4C_00", the trace line position on the right side where the tracing is started corresponds to the lateral wall (Lat) side, whereas the trace line position on the left side where the tracing is finished corresponds to the interventricular septum (IVS) side. Accordingly, by using these correspondence relationships, it is possible to realize a display that helps viewers understand the correspondence between the wall positions, by displaying the names of the walls such as "Lat" and "IVS" in the vicinity of the trace lines.

Next, an example will be discussed in which, by using the 2DT application as described above, the left atrium (LA), which has an upside-down relationship on the screen with the left ventricle (LV), is to be analyzed as a region of interest. When the endocardium of the left atrium (LA) is traced in the "A4C_00" image in the same manner as with the left ventricle (LV), because of the counterclockwise operation configuration, the tracing process is started from the annulus of the heart valve on the interventricular septum on the left side, routed through the pulmonary vein inflow section serving as the cardiac apex of the left atrium (LA), to the annulus of the heart valve on the lateral wall on the right side (see the broken line in the upper left section of FIG. 3). In this situation, the left and the right directions in the display of the corresponding wall position are inverted from those in the image of the left ventricle (LV). Accordingly, the lateral wall (Lat) side and the interventricular septum (IVS) side are each in the opposite position, compared to the actual left atrium (LA), as illustrated in the drawing.

To cope with this situation, as illustrated in the lower left section of FIG. 3, the display scheme of "A4C_10" is applied by which the y-direction is inverted, without changing the x-direction. When the left atrium (LA) is traced in the "A4C_10" image, as indicated by the solid line, it is possible to achieve the same relationship as that in the situation where the left ventricle (LV) is traced by using the "A4C_00" image. Accordingly, it is possible to provide the same operation configuration also for the left atrium (LA). In addition, it is possible to display the names of the walls in the correct positional relationship. This advantageous effect is achieved by cancelling the inversion of the up-and-down directions between the left ventricle (LV) and the left atrium (LA) in the acquisition within the two-dimensional data space, by realizing the upside-down display, in advance, with the coordinate systems of the data spaces.

Next, as supplementary information, a situation with the "A4C_11" image will also be explained, which is another possible example when the x-direction is inverted. As illustrated in the lower right section of FIG. 3, the "A4C_11" image is based on the display scheme by which not only the y-direction but also the x-direction of the "A4C_00" image is inverted. According to this display scheme, the "A4C_00" image has been rotated by 180 degrees with respect to the center of the image, and thus the image provides a page-front side view without a mirror-image inversion. Accordingly, because the positional relationship between the left side and the right side during the tracing process remains the same as that in the "A4C_00" image, this display scheme is not suitable for an analysis of the left atrium (LA), although the y-direction has been inverted.

As explained herein, in the two-dimensional examples, because there are two possible types of directional axes (i.e., one for the x-direction and the other for the y-direction), there are four possible inverted coordinate systems that are available, depending on whether or not the inversion is arranged on each of the axis. Further, an image of a page-front side view and an image of a page-rear side view correspond to a right-hand system and a left-hand system, while these two images are in the relationship of a mirror-image inversion. In the examples in FIG. 3, the images "A4C_00" and "A4C_11" correspond to the right-hand system, while the images "A4C_01" and "A4C_10" correspond to the left-hand system.

In this situation, the inversion in the up-and-down direction caused by the difference in the viewing direction (the scan direction) during the data acquisition brings about the mirror-image inversion in the data space. Consequently, for the purpose of solving the problems in the present embodiment, it is necessary to select such inverted coordinate systems that involve a mirror-image inversion when an inversion in the up-and-down direction has been arranged.

As explained above, between a body-surface probe and the TEE probe, the up-and-down direction is inverted with respect to the left ventricle (LV) or the right ventricle (RV) that serves as the same region of interest in the data spaces. Accordingly, a basic concept of the present embodiment is to utilize a situation where the relationship explained above with the left ventricle (LV) and the left atrium (LA) is similarly applicable. Further, one of the characteristics of the present embodiment lies in the realization of this effect in situations where the data space is three-dimensional.

When the data space is three-dimensional, a z-direction is also taken into consideration in addition to the x-direction and the y-direction in the two-dimensional example. In the present embodiment, the z-direction is a lateral direction orthogonal to the x-axis and is defined as an elevation direction. In three-dimensional examples, there are eight possible inverted coordinate systems in total, depending on whether or not an inversion is arranged on each of the three directional axes. In the situation where an A4C image is extracted as a display MPR image from a three-dimensional data space, when the notation "A4C_zyx" is used similarly to the example in FIG. 3 to express whether an inversion has been arranged or not with "1" and "0", respectively, the eight coordinate systems that are possibly available can be expressed as "A4C_000", "A4C_001", "A4C_010", "A4C_011", "A4C_100", "A4C_101", "A4C_110", and "A4C_111". In this situation, the coordinate systems that are possibly available when the y-direction, which corresponds to the up-and-direction of the display screen, is inverted (i.e., y=1) can be expressed as "A4C_z1x". Accordingly, the MPR images subject to selection are based on the four possible inverted coordinate systems expressed in (a) to (d) presented below:

(a) "A4C_010"
(b) "A4C_011"
(c) "A4C_110" and
(d) "A4C_111".

In this situation, (d) denotes a coordinate system obtained by rotating, by 180 degrees, the display scheme of "A4C_000" which has no inversion and is therefore not suitable for the purpose of the present embodiment. Further, (a) is obtained by inverting only the y-direction so that the positional relationship between the left side and the right side with respect to the two types of orientation directions is unchanged from that in the display scheme of "A4C_000" and is therefore not suitable for the purpose of the present embodiment.

Consequently, the two coordinate systems (b) and (c) are the mirror-image inverted coordinate systems that are both suitable for the purpose of the present embodiment. It is an object of the present embodiment to determine which one of these two candidates of inverted coordinate systems should be selected. The following sections will specifically explain a solution to this problem.

In the coordinate system (b), the y-direction and the x-direction have been inverted, and the z-direction has not been inverted. In other words, the x-y plane is viewed from the page-rear side, whereas the z-y plane remains to be viewed from the page-front side. In this situation, based on the assumption that the x-y plane corresponds to the position of an A4C image, the z-y plane is a cross-sectional plane orthogonal to the A4C image. The cross-sectional plane corresponds to a position in the middle of an A2C image and an A3C image, but will hereinafter be referred to as a "quasi-A2C image", for the sake of convenience. When the x-y plane corresponds to an A4C image, the y-direction corresponds to (or ideally equals to) the central axis extending in the long-axis direction and connecting the cardiac apex to the two annuli of the heart valves (see FIG. 3), while a ventricle is used as a region of interest. Accordingly, when the central axis of the ventricle is used as the axis of rotation, a positional relationship is exhibited where the quasi-A2C image is located in the position obtained by rotating the A4C image by 90 degrees.

In this situation, in the coordinate system (c), the y-direction and the z-direction have been inverted, whereas the x-direction has not been inverted. In other words, the quasi-A2C image representing the z-y plane is viewed from the page-rear side, whereas the A4C image representing the x-y plane remains to be viewed from the page-front side. As explained with the two-dimensional examples (see FIG. 3), for the purpose of maintaining the operability of the application, it is required to not invert the left-and-right relationship even when the up-and-down relationship is inverted. Accordingly, when an A4C image is extracted to realize an MPR display, (c) is the coordinate system that should be selected.

Further, on the basis of the orthogonal relationship between the A4C image and the quasi-A2C image, when a quasi-A2C image is extracted to realize an MPR display, (b) is the coordinate system that should be selected. These two coordinate systems are in such a relationship where the x-direction and the z-direction are interchanged by a 90-degree rotation that uses the y-direction as the axis of rotation. The following sections will explain how this relationship is interpreted in a three-dimensional data space obtained by a 3D-TEE probe configured to be able to acquire three-dimensional data.

Figure 4:
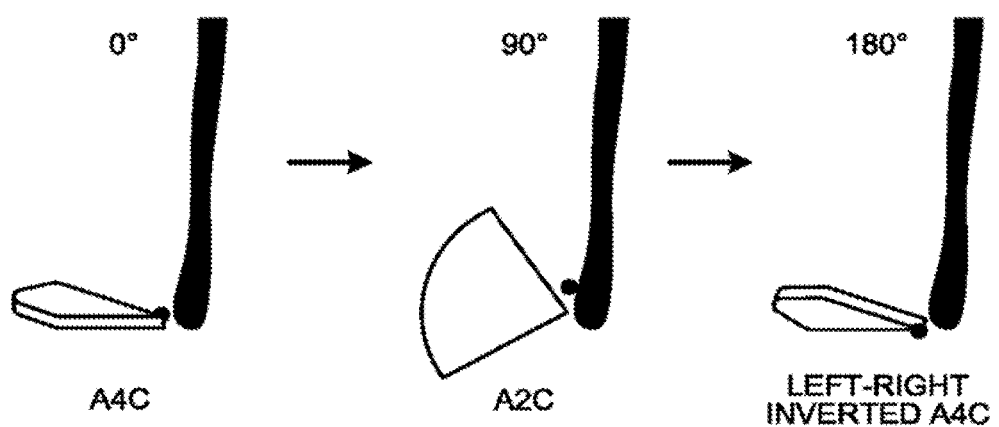
FIG. 4 is a drawing for explaining a positional relationship between rotation angles of the TEE probe and cross-sectional planes formed thereby.

Before 3D-TEE probes were developed, examples of available TEE probes included a multi-plane TEE probe configured to mechanically rotate the surface of transducer elements (corresponding to the plane surface used for obtaining a cross-sectional plane) structured with a one-dimensional array. When such a multi-plane TEE probe is used, because the directional axis of the ultrasound probe is limited by the esophagus, the positional relationship of the heart displayed in an output 2D image is kept in correspondence with the rotation angle of the surface of transducer elements. For example, as illustrated in FIG. 4, for an A4C image corresponding to the rotation angle of 0 degrees, a plane at an angle of 135 degrees is defined as a reference cross-sectional plane of a long-axis image (corresponding to an A3C image). In this situation, because the left-and-right direction is also uniquely determined, the plane at 180 degrees corresponds to the left-right inverted image (the "A4C_11" image in FIG. 3) of the A4C image. FIG. 4 is a drawing for explaining the positional relationship between rotation angles of the TEE probe and the cross-sectional planes formed thereby.

Further, when a 3D-TEE probe structured with a two-dimensional array is used, although it is possible to arbitrarily set the scan direction by performing an electronic scan, the restriction caused by the esophagus is the same. In addition, because 3D-TEE probes with a two-dimensional array were developed later, the information about the rotation angles defined for multi-plane TEE probes keeps being used without any change.

The relationship between the rotation angles and the cross-sectional planes is easy to understand with reference to FIG. 4. Similarly, even with 3D-TEE probes configured to be able to acquire three-dimensional data, when an observed cross-sectional plane corresponding to a rotation angle is imagined as an MPR image, it is easy to understand the left-and-right direction in the three-dimensional data space.

Figure 5:
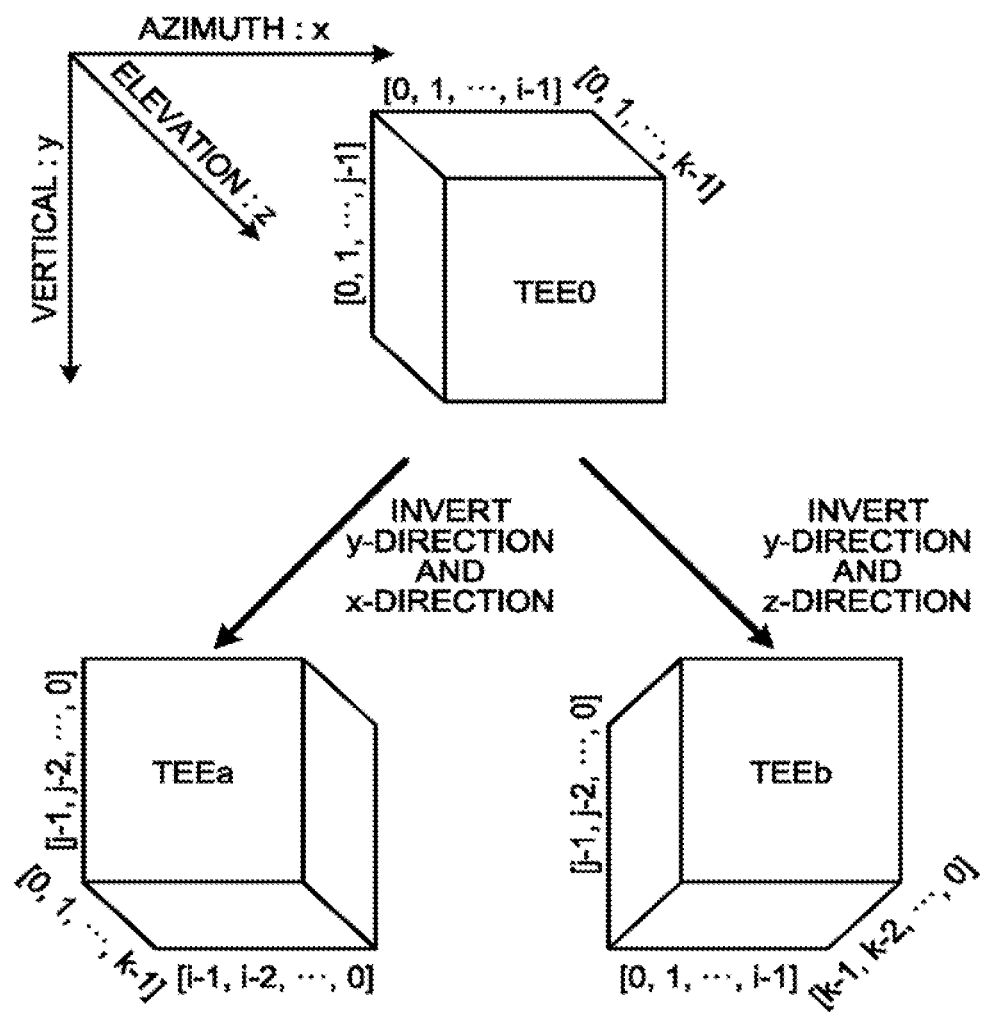
FIG. 5 is a drawing for explaining data spaces of volume data.

With reference to FIG. 5, the data space (the three-dimensional data space) of volume data will be explained. FIG. 5 is a drawing for explaining the data space of the volume data. The notation "TEE0" in FIG. 5 denotes a three-dimensional data space corresponding to the original coordinate system that has not been inverted. The notation "TEE0" denotes the three-dimensional data space in which pieces of data such as $[0, 1, \ldots, i-1]$ of which the quantity is equal to i are arranged in the x-direction (the azimuth direction) in the stated order, while pieces of data such as $[0, 1, \ldots, j-1]$ of which the quantity is equal to j are arranged in the y-direction (the vertical direction) in the stated order, and pieces of data such as $[0, 1, \ldots, k-1]$ of which the quantity is equal to k are arranged in the z-direction (the elevation direction) in the stated order.

First, when the rotation angle is 0 degrees, the A4C image substantially corresponds to the x-y plane. In this situation, the word "substantially" is used to cover the possibility that, when the positioning of the TEE probe head is adjusted, it may be difficult in some situations to define the y-direction so as to be perfectly in parallel to the central axis of the A4C image due to the interference of the esophagus. Although there is a restriction, three-dimensional data is acquired during actual TEE examinations in such a manner that the y-direction extends as close as possible to parallel to the central axis, so that an A4C image is acquired as a reference cross-sectional plane corresponding to the rotation angle of 0 degrees.

When we imagine increasing the rotation angle little by little, the position of the A4C image in the three-dimensional data space also rotates in accordance with the rotation angle. Eventually, when the rotation angle is equal to 90 degrees, the position of the quasi-A2C image corresponds to the x-y plane. This point in time corresponds to the abovementioned situation where the x-direction and the z-direction have been interchanged by the 90-degree rotation. The left side and the right side of the observed cross-sectional plane replace each other, while the rotation angle of 90 degrees serves as the turning point. It is imagined that, when the rotation angle reaches 180 degrees, a left-right inverted image of the A4C image corresponds to the x-y plane.

Accordingly, the ultrasound diagnosis apparatus 1 according to the first embodiment is configured to determine the positional relationship between the TEE probe and the patient P according to the rotation angle of the TEE probe. In other words, the ultrasound diagnosis apparatus 1 according to the first embodiment is configured to set a three-dimensional coordinate system on the basis of the positional relationship between the TEE probe and the patient P in such a manner that, among the three directions structuring the three-dimensional coordinate system of the volume video data, a first direction corresponding to the up-and-down direction of the display screen is inverted and that one selected from between a second direction and a third direction, which are the other directions among the three directions besides the first direction, is also inverted. For example, the ultrasound diagnosis apparatus 1 is configured to set the three-dimensional coordinate system on the basis of the rotation angle of the TEE probe observed at the time of the acquisition of pieces of volume data included in the volume video data.

More specifically, the ultrasound diagnosis apparatus 1 automatically selects an inverted coordinate system, by using information about the rotation angle of the TEE probe observed at the time of the acquisition of the volume data. For example, when the rotation angle of the TEE probe is equal to or larger than 0 degrees and smaller than 90 degrees, the ultrasound diagnosis apparatus 1 selects volume data in the inverted coordinate system "TEEb" obtained by inverting the y-direction and the z-direction (see the lower right section of FIG. 5). As another example, when the rotation angle of the TEE probe is in the range from 90 degrees to 180 degrees inclusive, the ultrasound diagnosis apparatus 1 selects volume data in the inverted coordinate system "TEEa" obtained by inverting the y-direction and the x-direction (see the lower left section of FIG. 5).

In this regard, in the present embodiment, to "invert" means to rearrange the order so that the pieces of data arranged in one direction are arranged in the reverse direction, on the axis in question. For example, when the y-direction is inverted, it means that the pieces of data such as [0, 1, ... j−2, j−1] of which the quantity is equal to j and which are arranged in the vertical direction in the stated order are rearranged into [j−1, j−2, ... 1, 0].

In the present embodiment, the example is explained in which the TEE rotation angle is defined in the range from 0 degrees to 180 degrees; however, it is also acceptable to expand the definition to the rotation angle in the range from 0 degrees to −180 degrees, which is obtained by extending the definition zone to the left-right inverted image (which corresponds to the definition used by Mayo Clinic explained with the A4C images) with respect to the range of the present example. However, in both situations, because the x-direction (the azimuth direction) and the z-direction (the elevation direction) that are orthogonal to each other replace each other by using the ±90-degree points as the turning points, it is desirable to switch between the inverted coordinate systems in units of 90 degrees (in units of 90 degrees as an absolute value).

To summarize the concept explained above, the first embodiment constitutes an example of an embodiment by which an appropriate inverted coordinate system suitable for the purpose (e.g., to acquire an observation MPR image oriented in a desirable direction) is selected on the basis of the acquired three-dimensional data, by recognition of the positional relationship between the heart rendered in the acquired three-dimensional data and the TEE probe while using the information about the "rotation angle of the TEE probe".

Figure 6:
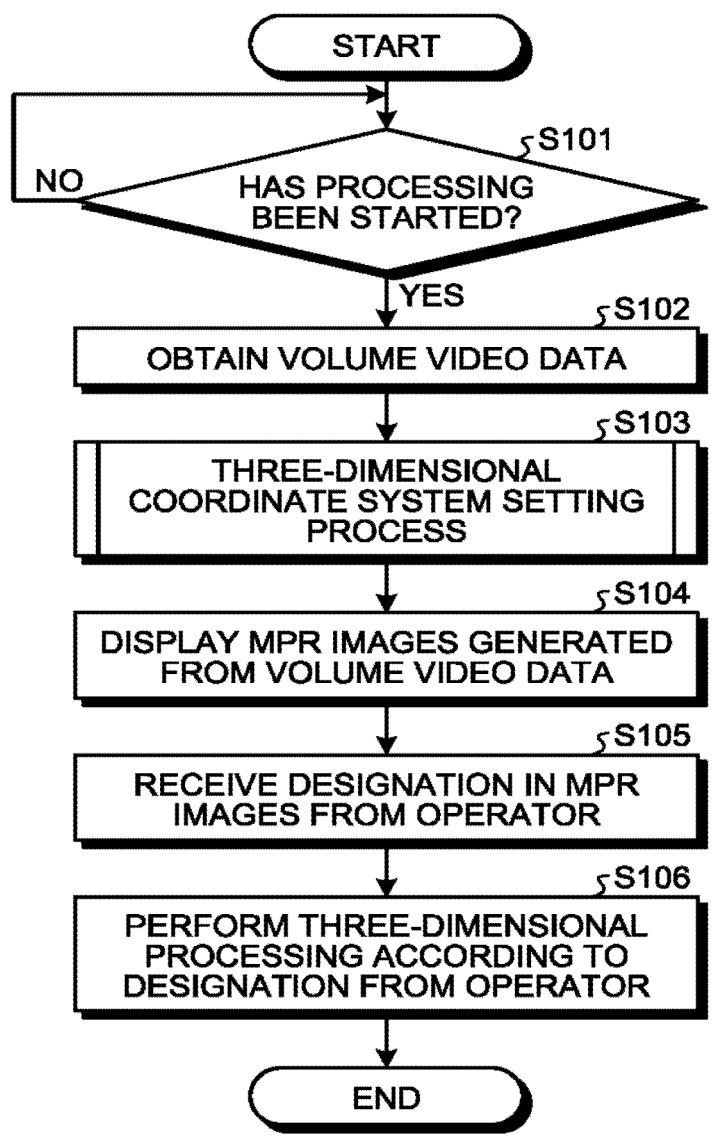
FIG. 6 is a flowchart illustrating a processing procedure performed by the ultrasound diagnosis apparatus according to the first embodiment.
Figure 7:
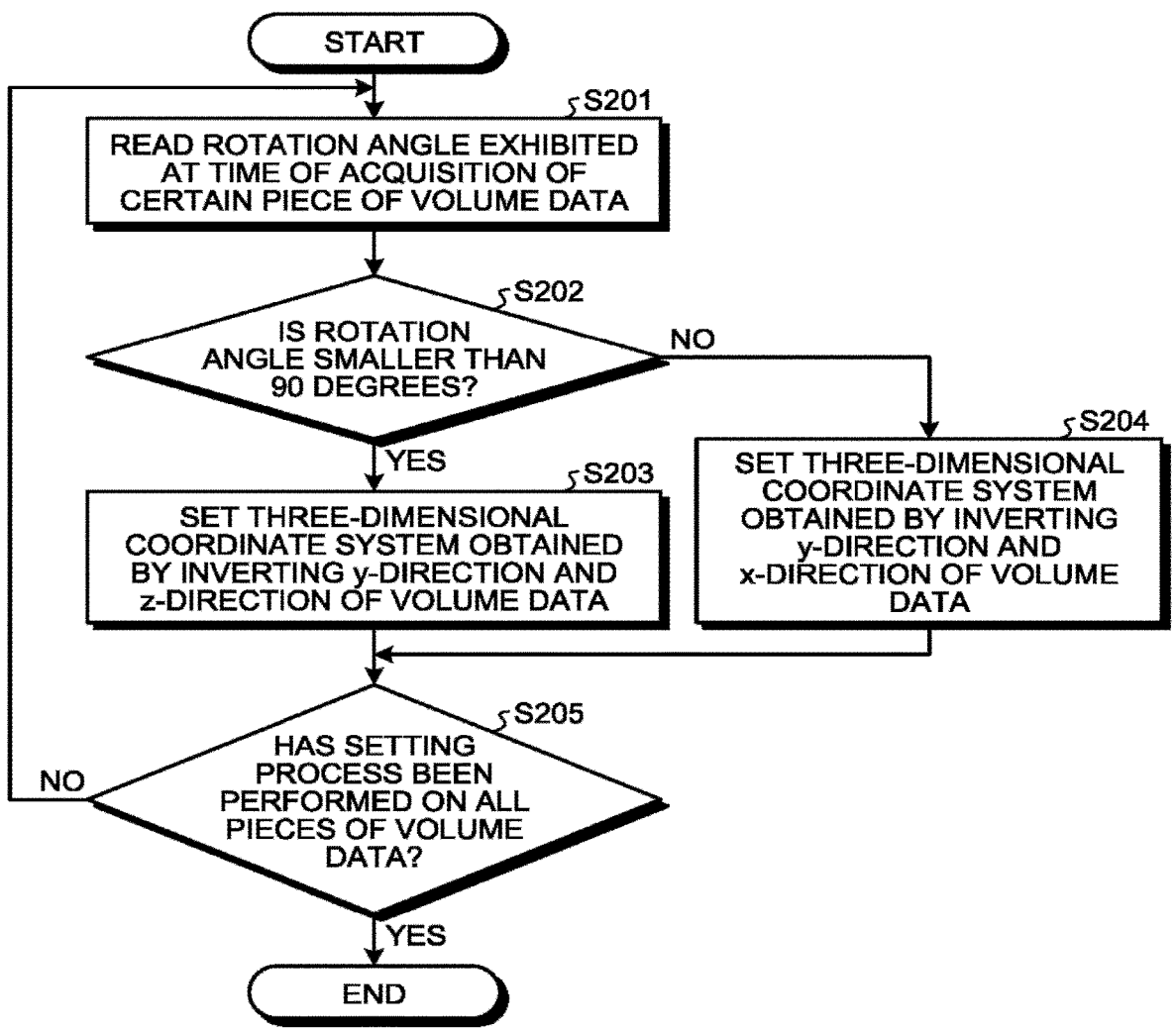
FIG. 7 is another flowchart illustrating the processing procedure performed by the ultrasound diagnosis apparatus according to the first embodiment.

Next, a processing procedure performed by the ultrasound diagnosis apparatus 1 according to the first embodiment will be explained, with reference to FIGS. 6 and 7. FIGS. 6 and 7 are flowcharts illustrating the processing procedure performed by the ultrasound diagnosis apparatus 1 according to the first embodiment. The processing procedure illustrated in FIG. 6 is started, for example, when an instruction is received from the operator indicating that three-dimensional processing (e.g., of a 3DT application) should be started. The processing procedure illustrated in FIG. 7 corresponds to the process at step S103 in FIG. 6.

At step S101, the processing circuitry 170 judges whether or not the processing has been started. For example, when having received, from the operator, an instruction indicating that a 3DT application should be started up, the processing circuitry 170 determines that the processing is started (step S101: Yes) and starts the processes at step S102 and thereafter. On the contrary, when the processing has not been started (step S101: No), the processes at step S102 and thereafter will not be started, and the processing functions of the processing circuitry 170 are in a standby state.

When the judgment result at step S101 is in the affirmative, the obtaining function 171 obtains volume video data at step S102. For example, the obtaining function 171 obtains the volume video data of the patient P acquired by the ultrasound probe 101 realized with a TEE probe. More specifically, the obtaining function 171 reads, from the image memory 150, the volume video data including pieces of volume data corresponding to a plurality of temporal phases.

At step S103, the setting function 172 performs a process of setting three-dimensional coordinate systems (hereinafter, "three-dimensional coordinate system setting process"). For example, on the basis of a positional relationship between the TEE probe and the patient P, the setting function 172 sets, with the volume video data, the three-dimensional coordinate system that matches the display orientation of image data of the patient P acquired by a body-surface probe. More specifically, on the basis of the positional relationship between the TEE probe and the patient P, the setting function 172 sets the three-dimensional coordinate system in such a manner that, among the three directions structuring the three-dimensional coordinate system of the volume video data, the first direction corresponding to the up-and-down direction of the display screen is inverted and that one selected from between the second direction and the third direction, which are the other directions among the three directions besides the first direction, is also inverted.

Next, the process at step S103 will be explained in detail, with reference to FIG. 7. At step S201, the setting function 172 reads the rotation angle observed at the time of the acquisition of a certain piece of volume data. The rotation angles of the TEE probe observed at the times of the acquisition of the pieces of volume data are, for example, each appended to a corresponding one of the pieces of volume data in advance. For example, with respect to an arbitrary one of the pieces of volume data corresponding to a plurality of temporal phases included in the volume video data, the setting function 172 reads information about the rotation angle of the TEE probe, out of the information appended to the piece of volume data.

At step S202, the setting function 172 judges whether or not the read rotation angle is smaller than 90 degrees. For example, when the rotation angle of the TEE probe observed at the time of the acquisition of the piece of volume data is smaller than 90 degrees (equal to or larger than 0 degrees and smaller than 90 degrees) (step S202: Yes), the setting function 172 performs the process at step S203. On the contrary, when the rotation angle of the TEE probe observed at the time of the acquisition of the piece of volume data is equal to or larger than 90 degrees (in the range from 90 degrees to 180 degrees inclusive) (step S202: No), the setting function 172 performs the process at step S204.

At step S203, the setting function 172 sets a three-dimensional coordinate system obtained by inverting the y-direction and the z-direction of the volume data. In other words, when the rotation angle of the TEE probe is equal to or larger than 0 degrees and smaller than 90 degrees, the setting function 172 selects the volume data in the inverted coordinate system "TEEb" obtained by inverting the y-direction and the z-direction (see the lower right section of FIG. 5).

At step S204, the setting function 172 sets a three-dimensional coordinate system obtained by inverting the y-direction and the x-direction of the volume data. In other words, when the rotation angle of the TEE probe is in the range from 90 degrees to 180 degrees inclusive, the setting function 172 selects the volume data in the inverted coordinate system "TEEa" obtained by inverting the y-direction and the x-direction (see the lower left section of FIG. 5).

At step S205, the setting function 172 judges whether the setting process has been performed on each of all the pieces of volume data. For example, the setting function 172 judges whether or not a three-dimensional coordinate system has been set with respect to the pieces of volume data corresponding to all the temporal phases that are included in the volume video data. In this situation, when the setting process has not been performed on all the pieces of volume data (step S205: No), the setting function 172 returns to the process at step S201 and repeatedly performs the processes in FIG. 7 until the setting process has been performed on all the pieces of volume data. On the contrary, when the setting process has been performed on each of all the pieces of volume data (step S205: Yes), the setting function 172 inputs the volume video data set with the three-dimensional coordinate systems to the application that performs the three-dimensional processing (the 3DT application in the example in FIG. 6) and thus ends the three-dimensional coordinate system setting process.

At step S104, the display controlling function 173 causes one or more MPR images generated from the volume video data to be displayed. For example, the display controlling function 173 generates an A4C image and an A2C image from a piece of volume data corresponding to an R-wave phase that is among the pieces of volume video data that have been set with the three-dimensional coordinate systems by the setting function 172. After that, the display controlling function 173 causes the display 103 to display the generated A4C and A2C images.

In this situation, with the piece of volume data corresponding to the R-wave phase, such a three-dimensional coordinate system is set that is obtained by inverting the y-direction of the volume data and further inverting either the z-direction or the x-direction depending on the rotation angle of the TEE probe observed at the time of the acquisition. Accordingly, the up-and-down direction and the left-and-right direction of the MPR images (the A4C image and the A2C image) generated from the piece of volume data corresponding to the R-wave phase substantially match the up-and-down direction and the left-and-right direction of MPR images derived from a commonly-used body-surface probe. Consequently, the operator is able to browse the displayed MPR images with perception that is substantially the same as perception for the up-and-down direction and the left-and-right direction of the MPR images derived from the commonly-used body-surface probe.

At step S105, the receiving function 174 receives a designation made by the operator in any of the MPR images. For example, within the A4C image displayed on the display 103, the operator performs an operation to trace the endocardium of the left ventricle (LV).

At step S106, the calculating function 175 performs three-dimensional processing according to the designation made by the operator. For example, in accordance with the operation performed by the operator, the calculating function 175 traces the endocardium of the left ventricle (LV). Further, the calculating function 175 calculates movement information of the left ventricular endocardium through a 3DT process by tracking the position of the traced endocardium over a plurality of temporal phases. To the 3DT process performed by the calculating function 175, it is possible to apply any conventionally-known technique.

In this situation, the up-and-down direction and the left-and-right direction of the MPR images derived from the TEE probe substantially match the up-and-down direction and the left-and-right direction of MPR images derived from a commonly-used body-surface probe. For this reason, even when the designation is received from the operator within the MPR images derived from the TEE probe, the calculating function 175 is able to perform the three-dimensional processing while using any conventional application that is designed to analyze volume data derived from a body-surface probe.

The contents of the explanation provided with reference to FIGS. 6 and 7 are merely examples, and possible embodiments are not limited to the above explanation. For example, the example is explained with reference to FIG. 7 in which the three-dimensional coordinate system setting process is performed on each of the pieces of volume data corresponding to all the temporal phases included in the volume video data; however, possible embodiments are not limited to this example. For instance, when the operator has designated a time period subject to the processing (e.g., a time period corresponding to one heartbeat), it is sufficient to set three-dimensional coordinate systems for the temporal phases included in the time period.

As explained above, in the ultrasound diagnosis apparatus 1 according to the first embodiment, the obtaining function 171 is configured to obtain the volume video data of the patient acquired by the transesophageal echocardiography probe. Further, on the basis of the positional relationship between the transesophageal echocardiography probe and the patient, the setting function 172 is configured to set, with the volume video data, the three-dimensional coordinate system that matches the display orientation of image data of the patient acquired by a body-surface probe. Further, the display controlling function 173 is configured to cause the display screen to display the image data generated from the volume video data by using the set three-dimensional coordinate system. Further, the receiving function 174 is configured to receive, from the operator, the designation related to calculating the movement information in the region of interest of the patient, the designation being received in the image displayed on the display screen. Further, the calculating function 175 is configured to calculate the movement information by performing processing including a tracking process, while using the volume video data. With these arrangements, the ultrasound diagnosis apparatus 1 according to the first embodiment is able to make simple and convenient the three-dimensional processing performed on the image data acquired by the transesophageal echocardiography probe.

For example, among the three directions structuring the three-dimensional coordinate system of the volume data acquired by the TEE probe, the setting function 172 inverts the y-direction corresponding to the up-and-down direction of the display screen. Further, the setting function 172 switches between the two types of three-dimensional mirror-image inverted coordinate systems ("TEEa" and "TEEb") that are possibly available with respect to the volume video data when the y-direction is inverted, depending on whether or not the rotation angle of the TEE probe is equal to or larger than the predetermined angle (e.g., 90 degrees). With this arrangement, for each of the pieces of volume data corresponding to the temporal phases included in the volume video data, the ultrasound diagnosis apparatus 1 is able to automatically set a three-dimensional coordinate system in accordance with the rotation angle observed at the time of the acquisition of the piece of volume data. As a result, the operator is able to browse and manipulate the MPR images derived from the TEE probe with perception that is substantially the same as perception for MPR images derived from a commonly-used body-surface probe, without the need to be conscious of the inversions in the up-and-down direction and the left-and-right direction.

Further, the setting function 172 inputs the volume video data that has been set with the three-dimensional coordinate systems as a result of the abovementioned process, to the application that performs the three-dimensional processing (e.g., the 3DT application in the example in FIG. 6). As a result, the application that performs the three-dimensional processing is able to perform the processing on the volume video data derived from the TEE probe, while using the same display interface as that used for volume video data derived from a body-surface probe. Consequently, it is possible to apply conventional applications designed to analyze volume video data derived from a body-surface probe, also to the volume video data derived from the TEE probe. Accordingly, there is no need to newly develop an application for the purpose of analyzing the volume video data derived from the TEE probe. It is therefore possible to reduce development costs.

In this situation, unlike the left ventricle, the right ventricle has a bilaterally asymmetrical shape. For this reason, when an application that performs three-dimensional processing such as 3DT is applied to the right ventricle, if an image remaining upside down were used, a huge burden would be imposed on the setting operation performed by the operator. However, when the ultrasound diagnosis apparatus 1 according to the first embodiment is used, because it is possible to use any of the conventional applications without any modification, the present disclosure is particularly effective when three-dimensional processing is performed on the right ventricle.

Further, the information about the rotation angles of the TEE probe used by the setting function 172 when setting the three-dimensional coordinate systems is usually appended to image data acquired by TEE probes. Accordingly, the processes performed by the ultrasound diagnosis apparatus 1 according to the first embodiment are applicable to any volume video data that has already been acquired by a conventional TEE probe.

In the first embodiment, the example is explained in which the 3DT process is used as the three-dimensional processing performed on the volume data; however, possible embodiments are not limited to this example. It is possible to apply any conventional image processing process.

Second Embodiment

In the first embodiment described above, the example is explained in which, to select the inverted coordinate systems, the insight information is used by which the rotation angles of the TEE probe are assumed to be in one-to-one correspondence with the positional relationships between the heart rendered in the acquired volume data and the TEE probe; however, possible embodiments are not limited to this example. Accordingly, in a second embodiment, a process of setting three-dimensional coordinate systems by using information other than the rotation angles of the TEE probe will be explained.

For example, Patent Literature 4 (Japanese Patent Publication No. 2011-078625) discloses a method for obtaining a display MPR image used for a 3DT application, by using a technique with which the central axis being a longer axis is detected from the left ventricle serving as a region of interest while using volume data acquired by a body-surface probe, so that an MPR position of a reference cross-sectional plane (e.g., an A4C image) passing through the detected central axis is extracted while distinguishing the left-and-right direction (whether the image is viewed from the page-front side or the page-rear side). In the present embodiment, between a body-surface probe and the TEE probe, the up-and-down direction (the y-direction) is inverted, in the acquired three-dimensional data space. Accordingly, to correctly detect the position and the orientation of the central axis from a region of interest in the ventricle by using the volume data acquired by the TEE probe, it is necessary to perform the processing on the premise that the up-and-down direction (the y-direction) is inverted from that of the three-dimensional data space expected for the body-surface probe.

To cope with this situation, the ultrasound diagnosis apparatus 1 according to the second embodiment is configured to switch between the two types of three-dimensional mirror-image inverted coordinate systems that are possibly available when the y-direction of the volume data is inverted, on the basis of a reference cross-sectional plane of a region of interest detected from the volume data.

The ultrasound diagnosis apparatus 1 according to the second embodiment has the same configuration as that of the ultrasound diagnosis apparatus 1 illustrated in FIG. 1, although a part of the processes performed by the setting function 172 is different. Accordingly, in the second embodiment, the differences from the first embodiment will primarily be explained. Explanations of some of the elements that have the same functions as those explained in the first embodiment will be omitted.

Figure 8:
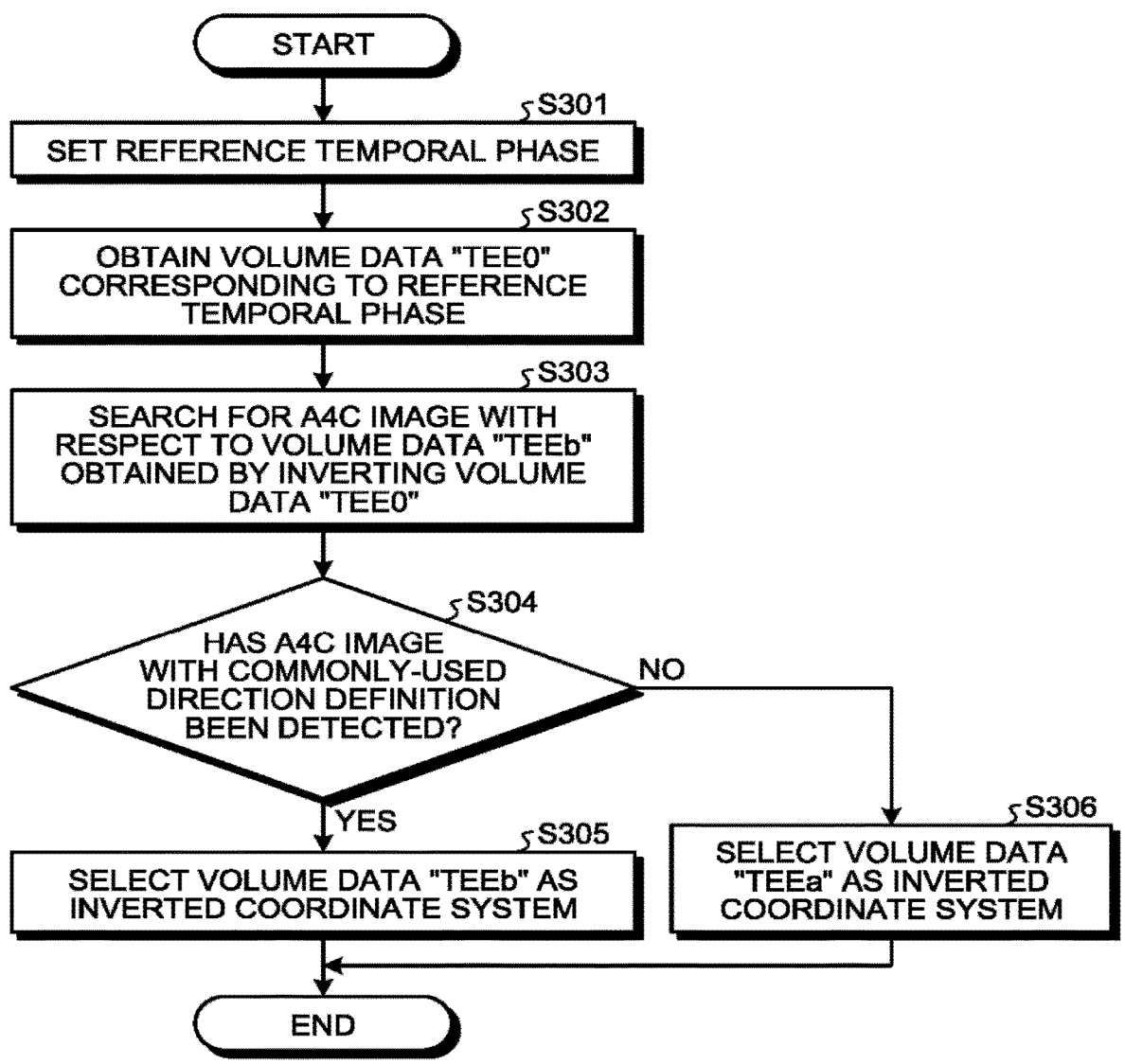
FIG. 8 is a flowchart illustrating a processing procedure performed by an ultrasound diagnosis apparatus according to a second embodiment.

A processing procedure performed by the ultrasound diagnosis apparatus 1 according to the second embodiment will be explained with reference to FIG. 8. FIG. 8 is a flowchart illustrating the processing procedure performed by the ultrasound diagnosis apparatus 1 according to the second embodiment. The processing procedure illustrated in FIG. 8 corresponds to the process at step S103 in FIG. 6. FIG. 8 illustrates the processing procedure by using the three-dimensional coordinate system of the volume data explained with reference to FIG. 5.

At step S301, the setting function 172 sets a reference temporal phase. For example, the setting function 172 sets an R-wave phase as the reference temporal phase. The reference temporal phase may be set in the application in advance or may manually be set by the operator after the application is started up.

At step S302, the setting function 172 obtains volume data "TEE0" corresponding to the reference temporal phase that was set. For example, from among pieces of volume video data corresponding to one heartbeat, the setting function 172 obtains a piece of volume data "TEE0" corresponding to the R-wave phase that was set. The piece of volume data obtained in this situation is "TEE0" in which none of the three directions structuring the three-dimensional coordinate system of the volume data has been inverted.

At step S303, the setting function 172 searches for an A4C image with respect to the piece of volume data "TEEb" obtained by inverting the piece of volume data "TEE0". For example, the setting function 172 generates the piece of volume data "TEEb" obtained by inverting the y-direction and the z-direction of the piece of volume data "TEE0". After that, the setting function 172 detects the central axis of the region of interest (e.g., the left ventricle) from the generated piece of volume data "TEEb". Subsequently, the setting function 172 generates a plurality of MPR images passing through the detected central axis from the piece of volume data "TEEb" and searches for an MPR image corresponding to an A4C image from among the plurality of generated MPR images. For example, by comparing the MPR images with dictionary data (shape database by machine learning) describing characteristics of A4C images while using a classifier, the setting function 172 detects the MPR image corresponding to an A4C image from among the plurality of MPR images.

At step S304, the setting function 172 judges whether or not an A4C image rendered with the commonly-used direction definition has been detected. For example, when an A4C image rendered with the commonly-used direction definition has been detected (step S304: Yes), the setting function 172 proceeds to the process at step S305. On the contrary, when not an A4C image rendered with the commonly-used direction definition but an A4C image rendered with the Mayo Clinic direction definition has been detected, for example, (step S304: No), the setting function 172 proceeds to the process at step S306. The judging process is performed by, for example, by performing a comparing process with the use of either a shape dictionary database describing characteristics of A4C images rendered with the commonly-used direction definition or a shape dictionary database describing characteristics of A4C images rendered with the Mayo Clinic direction definition.

At step S305, the setting function 172 selects the piece of volume data "TEEb" as an inverted coordinate system. For example, as a result of the search for an A4C image with respect to the piece of volume data "TEEb", when an A4C image rendered with the commonly-used direction definition has been detected, the setting function 172 selects the piece of volume data "TEEb" obtained by inverting the y-direction and the z-direction. In other words, the setting function 172 sets, with the piece of volume data, the three-dimensional coordinate system obtained by inverting the y-direction and the z-direction of the piece of volume data "TEE0".

At step S306, the setting function 172 selects the piece of volume data "TEEa" as an inverted coordinate system. For example, as a result of the search for an A4C image with respect to the piece of volume data "TEEb", when an A4C image rendered with the Mayo Clinic direction definition has been detected, the setting function 172 selects the piece of volume data "TEEa" obtained by inverting the y-direction and the x-direction. In other words, the setting function 172 sets, with the piece of volume data, the three-dimensional coordinate system obtained by inverting the y-direction and the x-direction of the piece of volume data "TEE0".

After that, the setting function 172 inputs the pieces of volume data that have been set with the three-dimensional coordinate systems, to the application that performs three-dimensional processing (the 3DT application in the example in FIG. 6) and thus ends the three-dimensional coordinate system setting process.

As explained above, in the ultrasound diagnosis apparatus 1 according to the second embodiment, the setting function 172 is configured to detect the central axis of the region of interest and the reference cross-sectional plane passing through the central axis, from the piece of volume data corresponding to at least one temporal phase among the pieces of volume data corresponding to the plurality of temporal phases included in the volume video data. After that, the setting function 172 is configured to set the three-dimensional coordinate systems on the basis of the central axis and the reference cross-sectional plane that were detected. More specifically, the setting function 172 is configured to switch between the two types of three-dimensional mirror-image inverted coordinate systems that are possibly available with respect to the volume video data obtained by inverting the y-direction, on the basis of the central axis and the reference cross-sectional plane. With these arrangements, the ultrasound diagnosis apparatus 1 according to the second embodiment is able to select the inverted coordinate systems by using the information about the left-and-right direction of the detected cross-sectional plane.

Third Embodiment

In a third embodiment, an example will be explained in which the orientation of a display MPR image is adjusted so that the up-and-down direction of the display MPR image derived from the TEE probe more accurately matches the up-and-down direction of an MPR image derived from a body-surface probe. The processes according to the third embodiment are applicable to each of the first and the second embodiments.

More specifically, the ultrasound diagnosis apparatus 1 according to the third embodiment is capable, as explained in the second embodiment, of detecting the orientation of the central axis of a region of interest within the data space of the volume data acquired by the TEE probe. Accordingly, the ultrasound diagnosis apparatus 1 according to the third embodiment is configured to adjust the orientation of the display MPR image by using the detected orientation of the central axis, when the image is applied to a 3DT application.

The ultrasound diagnosis apparatus 1 according to the third embodiment has the same configuration as that of the ultrasound diagnosis apparatus 1 illustrated in FIG. 1, although a part of the processes performed by the display controlling function 173 is different. Accordingly, in the third embodiment, the differences from the first embodiment will primarily be explained. Explanations of some of the elements that have the same functions as those explained in the first embodiment will be omitted.

Figure 9:
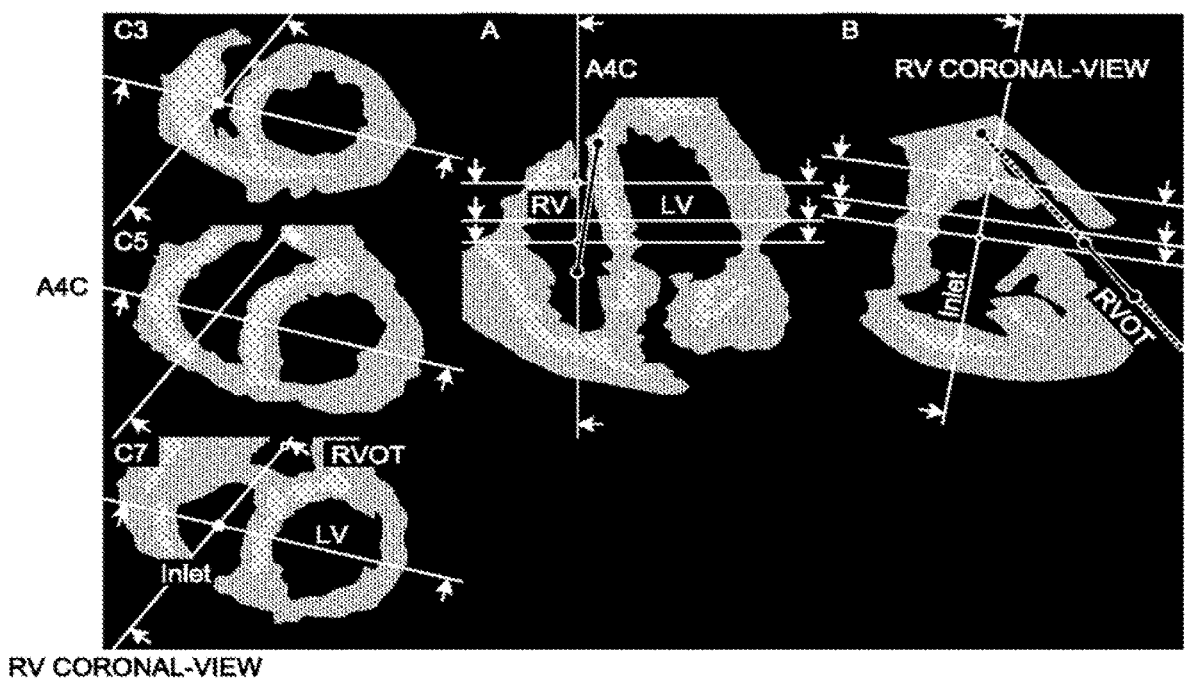
FIG. 9 is a drawing for explaining processes performed by an ultrasound diagnosis apparatus according to a third embodiment.
Figure 10:
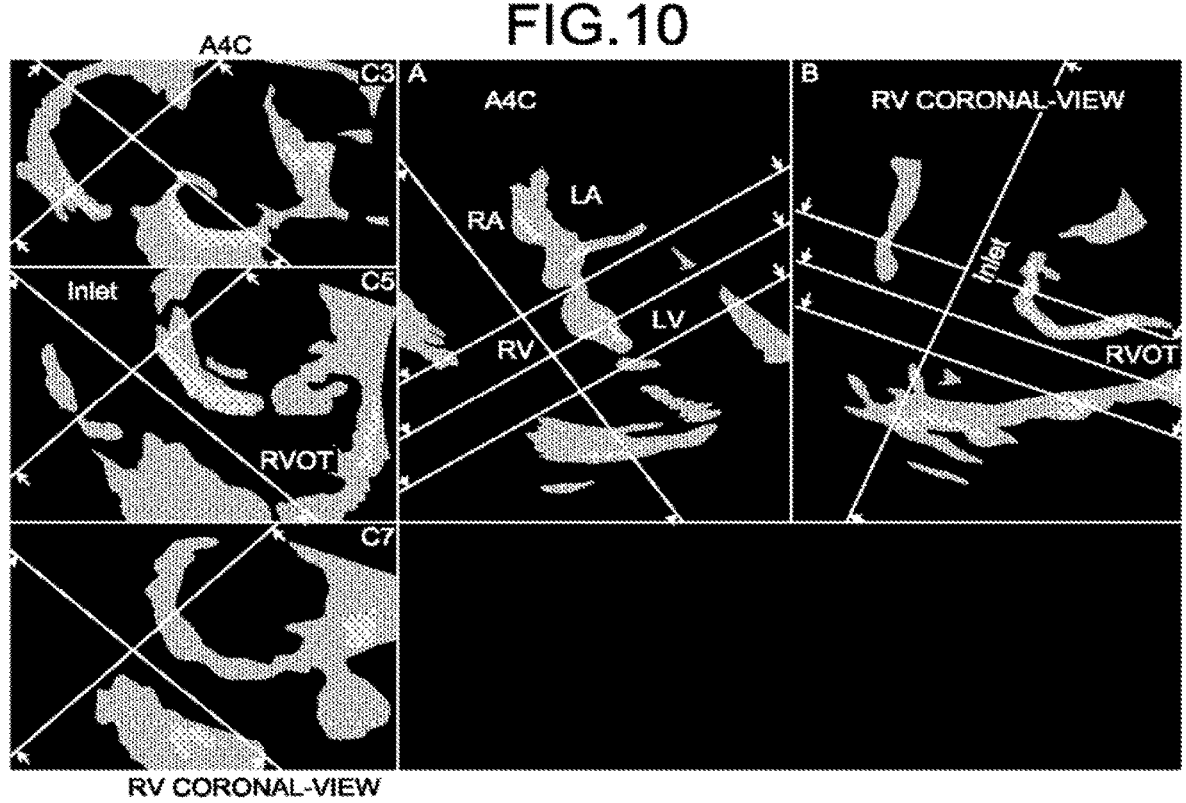
FIG. 10 is another drawing for explaining the processes performed by the ultrasound diagnosis apparatus according to the third embodiment.
Figure 11:
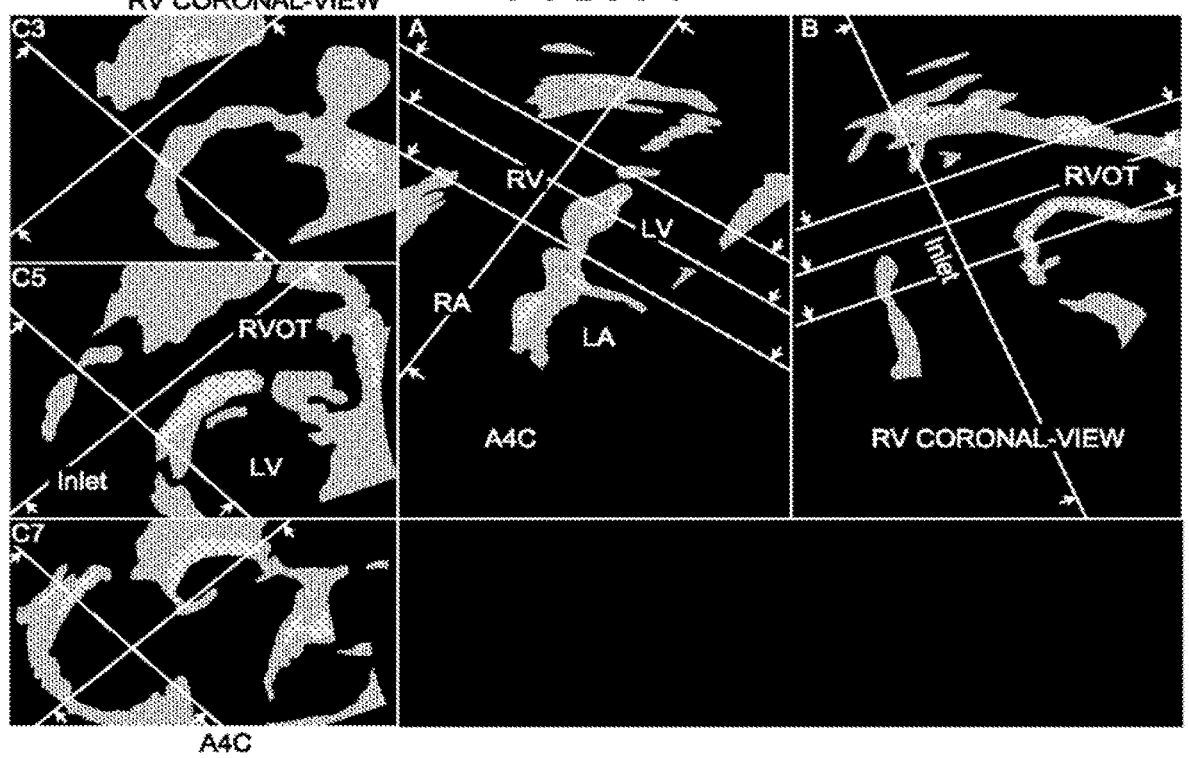
FIG. 11 is yet another drawing for explaining the processes performed by the ultrasound diagnosis apparatus according to the third embodiment.
Figure 12:
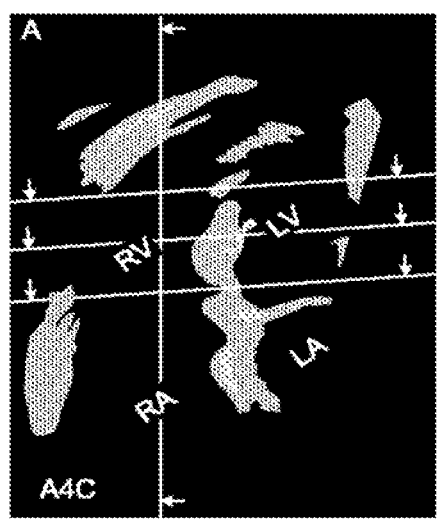
FIG. 12 is yet another drawing for explaining the processes performed by the ultrasound diagnosis apparatus according to the third embodiment.

Processes performed by the ultrasound diagnosis apparatus 1 according to the third embodiment will be explained, with reference to FIGS. 9 to 12. FIGS. 9 to 12 are drawings for explaining the processes performed by the ultrasound diagnosis apparatus 1 according to the third embodiment. FIG. 9 illustrates MPR images derived from a body-surface probe. FIGS. 10 to 12 illustrate MPR images derived from the TEE probe. Further, in FIGS. 9 to 12, the straight lines drawn in the MPR images each indicate a cross-section position of another MPR image. Further, the arrows placed next to each of the straight lines indicating a cross-section position indicate the direction in which the cross-section position is viewed. For example, in FIG. 9, the straight line drawn in the up-and-down direction on plane A indicates the cross-section position of plane B. It is indicated that plane B represents an MPR image obtained by viewing the site from the right-hand side in plane A.

FIG. 9 illustrates MPR images displayed by using an RV-3DT application that uses the right ventricle (RV) as a region of interest, while using volume video data acquired by a body-surface probe. In the example in FIG. 9, five MPR images are displayed for the purpose of setting a region of interest on the myocardium of the right ventricle (RV) subject to a tracking process. The long-axis view on plane A corresponds to an A4C image. The long-axis view on plane B represents an RV coronal view that renders the inflow tract ("Inlet") and the outflow tract ("RVOT") of the right ventricle at the same time. While using a body-surface probe, it is possible, as indicated in the A4C image in FIG. 9, to align the central axis with the height direction (the up-and-down direction) of the MPR screen while using the cardiac apex as the top site, by adjusting the manner in which the probe is kept in contact with the patient's body. While utilizing this characteristic, the RV-3DT application illustrated in FIG. 9 displays a straight line marker indicating the central axis of the right ventricle on plane A. The top position of the marker is arranged to be in a cardiac apex position, whereas the bottom position of the marker is arranged to be in a tricuspid valve center position. With these arrangements, the two positions serving as biological landmarks of the right ventricle (RV) are input to the application. In this situation, on the premise that the A4C image displayed on plane A is rendered by using the positional relationships illustrated in FIG. 9, by providing a position in the vicinity of the position illustrated in FIG. 9 as an initial position of the displayed marker, it is possible to reduce the operation range required by the input adjustment of the biological landmarks (the cardiac apex and the tricuspid valve) performed by the operator. It is therefore possible to provide operability that is simple and convenient.

In this situation, C3, C5, and C7 denote short-axis images on three levels related to a right ventricular region viewed from the cardiac apex side. Among these three images, in the C7 MPR image, which is closest to the tricuspid valve and the pulmonary valve, the inflow tract ("Inlet") of the right ventricle is rendered on the lower left side of the left ventricle (LV), whereas an outflow tract (RVOT) is rendered on the upper right side of the left ventricle (LV).

In contrast, when the TEE probe is used, although an MPR image corresponding to the rotation angle of 0 degrees is rendered as an A4C image as explained above, the central axis of the right ventricle does not necessarily match the up-and-down direction of the MPR image. In this regard, FIG. 10 illustrates five MPR images of a right ventricular region by using volume data acquired by the TEE probe.

FIG. 10 illustrates MPR images derived from the TEE probe and generated without performing the three-dimensional coordinate system setting process explained in the first and the second embodiments. As illustrated in FIG. 10 the MPR images have been inverted substantially in the up-and-down direction, compared to the MPR images derived from the body-surface probe illustrated in FIG. 9. Further, the capability of rendering in the surroundings of the right ventricular outflow tract (RVOT) is improved in comparison to the MPR images derived from the body-surface probe. Accordingly, it is observed that there is an advantage in performing the RV-3DT process by using the volume video data derived from the TEE probe. Further, in the A4C image (plane A) in FIG. 10, the central axis of the right ventricle is rendered at an angle (substantially at an angle of 40 degrees) with respect to the up-and-down direction of the screen.

FIG. 11 illustrates MPR images derived from the TEE probe and generated after performing the three-dimensional coordinate system setting process explained in the first and the second embodiments. In other words, the three-dimensional coordinate systems are set so as to invert the y-direction and to also invert one of the x- and z-directions, with respect to the three-dimensional data space used by the 3DT application.

For example, when the three-dimensional coordinate system setting process is not performed, as illustrated in FIG. 10, the positional relationship among the left ventricle (LV), the right ventricular inflow tract ("Inlet"), and the right ventricular outflow tract (RVOT) rendered on plane C5 has the left-and-right direction inverted, compared to the positional relationship on plane C7 derived from the body-surface probe illustrated in FIG. 9. In contrast, when the three-dimensional coordinate system setting process is performed, as illustrated in FIG. 11, the positional relationship among the left ventricle (LV), the right ventricular inflow tract ("Inlet"), and the right ventricular outflow tract (RVOT) rendered on plane C5 is the same as the positional relationship on plane C7 derived from the body-surface probe illustrated in FIG. 9. Further, it is also observed that, when the three-dimensional coordinate system setting process is performed, the arrows indicating the directions in which the cross-section positions are viewed are also rendered in the same directions as those with the MPR images derived from the body-surface probe.

Further, it is also indicated that, when the three-dimensional coordinate system setting process is performed, the positional relationships in the left-and-right direction of the A4C image on plane A and the RV coronal view on plane B are also the same as those in the MPR images derived from the body-surface probe. Accordingly, as illustrated in FIG. 11, by performing the three-dimensional coordinate system setting process, it is possible to apply the RV-3DT application to the volume video data derived from the TEE probe, with operability that is the same as operability experienced when the body-surface probe is used.

However, because the central axis of the right ventricle in the A4C images in FIG. 11 is at an angle with respect to the up-and-down direction of the display screen, if the above-mentioned marker were displayed (see FIG. 9) in the initial position expected in the image data derived from the body-surface probe, the range in which the operator needs to move the marker to adjust the positions of the biological landmarks (the cardiac apex and the tricuspid valve) would increase. In that situation, the operability would be degraded compared to the situation where a body-surface probe is used. To cope with this problem, the ultrasound diagnosis apparatus 1 according to the third embodiment is configured to improve the operability by using orientation information of the central axis detected from the volume data. In this situation, there are two possible methods for improving the operability as described below.

A first method is a method by which the display orientation of the MPR image is rotated with respect to the marker display position, so that the central axis matches the up-and-down direction of the display screen, by using the orientation information of the central axis of the region of interest. In other words, the display controlling function 173 is configured to adjust the orientation of the display image generated from the volume video data so that the central axis of the region of interest corresponds to the up-and-down direction of the display screen.

For example, as illustrated in FIG. 11, it is observed that the central axis of the A4C image generated after performing the three-dimensional coordinate system setting process is tilted at an angle of approximately 40 degrees in the 2 o'clock direction, compared to the central axis illustrated in FIG. 9. As explained in the first embodiment, the rotation angle of the TEE probe corresponds to the positional relationship of the heart rendered in the data space of the acquired volume data. Accordingly, it is expected that the tilting at an angle of 40 degrees is also true with other clinical data, with a relatively small error. Accordingly, it is possible to determine, in advance, an expected value (a correction rotation expected value) indicating by how many degrees the image should be tilted, in accordance with the setting of the rotation angle of each of the TEE probes. The correction rotation expected value is expressed as a value obtained by attaching an opposite sign to the aforementioned tilting angle of the central axis. For example, when the rotation angle of the TEE probe is 0 degrees, the correction rotation (tilting) expected value is set to −40 degrees. In that situation, as illustrated in FIG. 12, the display controlling function 173 rotates the A4C image derived from the TEE probe by −40 degrees. As a result, the display controlling function 173 is able to provide an initial display setting of the marker with which the adjustment range is small, in the same manner as with the A4C image derived from the body-surface probe.

A second method is a method by which, by using the orientation information of the central axis, the initial display position used for displaying the marker is rotated with respect to the display MPR image so as to match the central axis. In other words, the display controlling function 173 is configured to adjust the orientation of the initial display position used for displaying the marker, so that the initial display position used for displaying the marker corresponds to the central axis of the region of interest.

For example, after rotating, by 40 degrees, the initial display position used for displaying the marker illustrated in FIG. 9, the display controlling function 173 causes the initial display position to be displayed in the A4C image illustrated in FIG. 11. In this situation, the angle of rotation (40 degrees) is the value obtained by attaching an opposite sign to the abovementioned correction rotation (tilting) expected value. As a result, it is possible to prevent an increase in the range in which the operator needs to move the marker to adjust the biological landmarks (the cardiac apex and the tricuspid valve). It is therefore possible to provide operability that is the same as operability experienced when a body-surface probe is used.

A Modification Example of Third Embodiment

In the third embodiment, the example is explained in which either the MPR image or the initial display position for displaying the maker is rotated by using the correction rotation expected value; however, possible embodiments are not limited to this example. For instance, in place of the process using the correction rotation expected value, the ultrasound diagnosis apparatus 1 may perform the rotating and adjusting process that implements either the first method or the second method explained in the third embodiment, by using both the information about the rotation angle of the TEE probe and the orientation information of the central axis detected from the image data.

In this situation, the setting function 172 at first selects one of the two types of three-dimensional mirror-image inverted coordinate systems that are possibly available (i.e., TEEa and TEEb with respect to TEE0), by using the rotation angle of the TEE probe. The detecting process using the image data requires processing time for the detection. In addition, depending on the image quality of the acquired volume data, there is a possibility that the accuracy of the detecting process may be lowered. However, by using the rotation angle of the TEE probe, it is possible to alleviate such impacts.

Subsequently, a reference cross-sectional plane represented by an A4C image, for example, is automatically detected by using the volume data in the selected inverted coordinate system. In that situation, it is expected that an A4C image rendered with the commonly-used direction definition is contained in the vicinity of the x-y plane in the data space. It is therefore possible to improve the accuracy in detecting the orientation of the central axis and robustness for the image quality, by limiting search conditions used for detecting the orientation of the central axis. Further, by limiting the range in which the orientation of the central axis is searched, it is also possible to decrease the calculation time period required for the detection. Further, by using the detected orientation information of the central axis as the correction rotation expected value explained above, the display controlling function 173 performs the rotating and adjusting process that implements either the first method or the second method.

Fourth Embodiment

In the embodiments described above, the example is explained in which the ultrasound diagnosis apparatus 1 processes the volume video data derived from the TEE probe; however, possible embodiments are not limited to this example. For instance, the ultrasound diagnosis apparatus 1 is further capable of processing volume video data derived from a body-surface probe. The ultrasound diagnosis apparatus 1 is capable of performing, as appropriate, a three-dimensional inverted coordinate system setting process, in accordance with the type of the ultrasound probe 101 used for acquiring the volume video data subject to the processing.

For example, information about the type of the ultrasound probe 101 used for acquiring volume video data is configured into the acquired volume video data as appended information. Further, when inputting the volume video data to an application that performs three-dimensional processing, the processing circuitry 170 refers to the appended information and identifies the information about the type of the ultrasound probe 101. In this situation, when the volume video data is derived from a body-surface probe, the processing circuitry 170 inputs the volume video data to the application, without performing the three-dimensional inverted coordinate system setting process. On the contrary, when the volume video data is derived from the TEE probe, the processing circuitry 170 inputs the volume video data to the application, after performing the three-dimensional inverted coordinate system setting process.

In other words, in the ultrasound diagnosis apparatus 1 according to the fourth embodiment, the obtaining function 171 is further configured to obtain the volume video data derived from the body-surface probe. After that, when volume video data derived from the body-surface probe is obtained, the setting function 172 does not set any three-dimensional inverted coordinate system with the obtained volume video data. On the contrary, when volume video data derived from the TEE probe is obtained, the setting function 172 sets a three-dimensional inverted coordinate system with the obtained volume video data.

With these arrangements, even when mutually the same three-dimensional processing application is used for the TEE probe and for the body-surface probe, the ultrasound diagnosis apparatus 1 is configured to automatically judge whether or not the three-dimensional inverted coordinate system setting process is to be performed, by using the information appended to the volume video data. Accordingly, the operator is able to use the application without being conscious of whether or not an inversion in the up-and-down direction has been arranged or the type of the ultrasound probe, by simply selecting the volume video data to be input to the application.

Fifth Embodiment

In the embodiments described above, the example is explained in which the volume video data derived from the TEE probe is applied to the application that performs the three-dimensional processing such as a 3DT process; however, possible embodiments are not limited to this example. For instance, the ultrasound diagnosis apparatus 1 may realize only the MPR display with the volume video data on which the three-dimensional inverted coordinate system setting process has been performed, without inputting the volume video data to an application that performs three-dimensional processing. In that situation, it is desirable to realize the MPR display by selecting a reference cross-sectional plane. There is no problem that the volume video data in this case is not limited to the data format converted to the Cartesian coordinate system as shown in FIG. 5. Raw data format (coordinate system determined by the scan angle and the depth of the ultrasonic wave) as volume video data is also available with using the concept of inverting coordinate system based on this invention. In the 3DT processing, the volume data format in the Cartesian coordinate system is convenient, whereas in a general MPR image rendering processing, it is directly converted from volume data in raw data format.

For example, the TEE probe having a rotation angle of 0 degrees corresponds to an A4C image. When the three-dimensional inverted coordinate system setting process is not performed, the cardiac apex is rendered on the lower side of the screen, while the left ventricle is rendered on the right side of the screen, and the right ventricle is rendered on the left side of the screen, within the A4C image, as illustrated in FIG. 10. In this situation, by internally selecting the volume data "TEEb" by performing the three-dimensional inverted coordinate system setting process, it is possible, as illustrated in FIG. 11, to provide an MPR image of which the up-and-down direction and the left-and-right direction on the display screen are the same as those of an MPR image derived from a body-surface probe.

In other words, in the ultrasound diagnosis apparatus 1 according to the fifth embodiment, the obtaining function 171 is configured to obtain the volume data of the patient P acquired by the TEE probe and the rotation angle of the TEE probe observed at the time of the acquisition of the volume data. The setting function 172 is configured to set, with the volume data derived from the TEE probe, the three-dimensional coordinate system that matches the display orientation of the image data of the patient acquired by the body-surface probe, on the basis of the rotation angle of the TEE probe. The display controlling function 173 is configured to cause the display screen to display the image data generated from the volume data by using the three-dimensional coordinate system. Accordingly, by using the direction definition explained above when realizing the MPR display with the volume data acquired by the 3D-TEE probe, it is expected that consensus is easily achieved while interpreting and using the MPR images in diagnosis processes in a universal manner, regardless of whether an application that performs three-dimensional processing is being used or not.

Other Embodiments

It is acceptable to carry out the present disclosure in various different modes other than those explained in the embodiments above.

An Image Processing Apparatus

For example, in the embodiments described above, the example is explained in which the various types of processing functions that perform the three-dimensional inverted coordinate system setting process are applied to the ultrasound diagnosis apparatus 1; however, possible embodiments are not limited to this example. For instance, the various types of processing functions that perform the three-dimensional inverted coordinate system setting process may be applied to an image processing apparatus.

Figure 13:
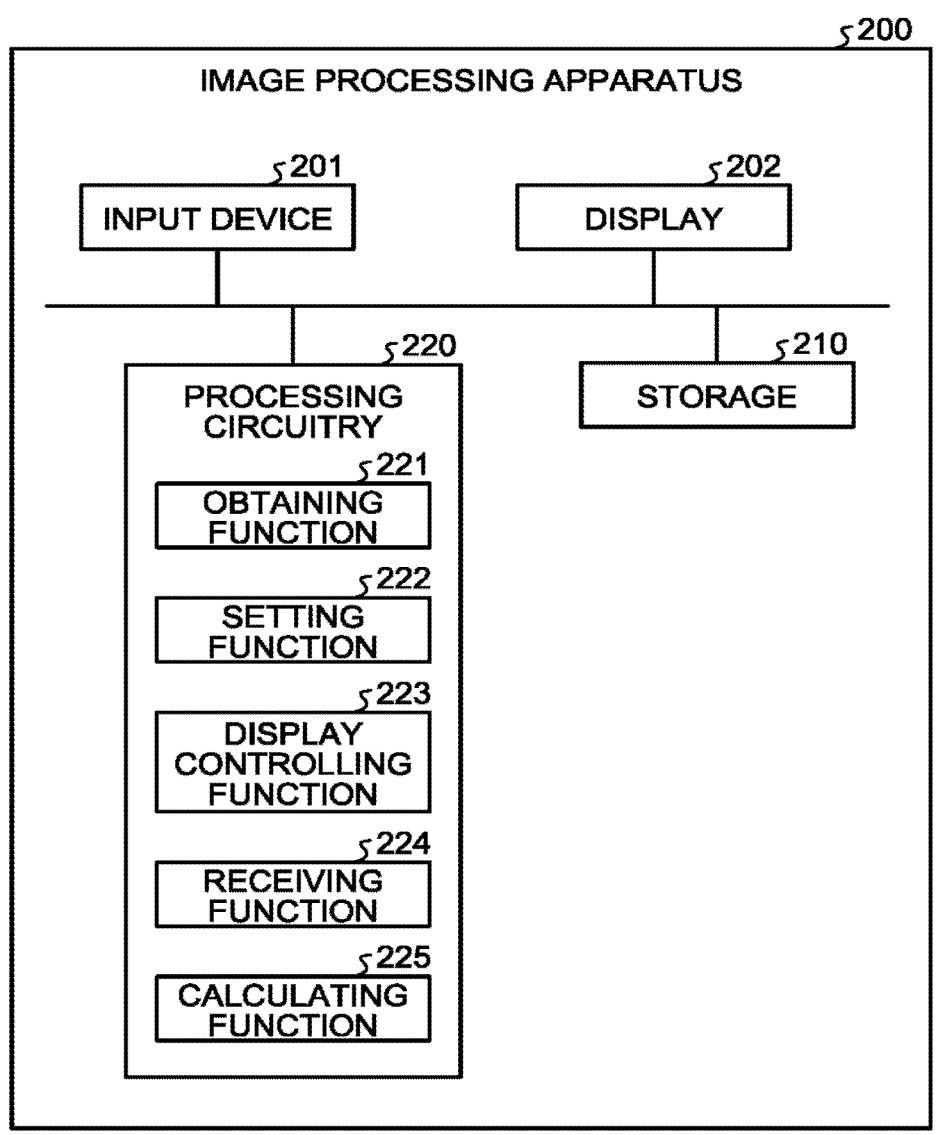
FIG. 13 is a block diagram illustrating an exemplary configuration of an image processing apparatus according to another embodiment.

A configuration of an image processing apparatus 200 according to another embodiment will be explained with reference to FIG. 13. FIG. 13 is a block diagram illustrating an exemplary configuration of the image processing apparatus 200 according to said another embodiment.

As illustrated in FIG. 13, the image processing apparatus 200 includes an input device 201, a display 202, storage 210, and processing circuitry 220. The input device 201, the display 202, the storage 210, and the processing circuitry 220 are connected together so as to be able to communicate with one another.

The processing circuitry 220 executes an obtaining function 221, a setting function 222, a display controlling function 223, a receiving function 224, and a calculating function 225. In this situation, processing functions of the obtaining function 221, the setting function 222, the display controlling function 223, the receiving function 224, and the calculating function 225 are capable of performing the same processes as those performed by the processing functions of the obtaining function 171, the setting function 172, the display controlling function 173, the receiving function 174, and the calculating function 175 illustrated in FIG. 1.

In other words, in the image processing apparatus 200, the obtaining function 221 is configured to obtain the volume video data of the patient acquired by the transesophageal echocardiography probe. Further, the setting function 222 is configured to set, with the volume video data, a three-dimensional coordinate system that matches the display orientation of image data of the patient acquired by a body-surface probe, on the basis of the positional relationship between the transesophageal echocardiography probe and the patient. Further, the display controlling function 223 is configured to cause a display screen to display image data generated from the volume video data by using the set three-dimensional coordinate system. Further, the receiving function 224 is configured to receive, from the operator, a designation related to calculating movement information in the region of interest of the patient, the designation being received in the image displayed on the display screen.

Further, the calculating function 225 is configured to calculate the movement information by performing processing including a tracking process, while using the volume video data. With these arrangements, the ultrasound diagnosis apparatus 1 according to said another embodiment is able to make simple and convenient the three-dimensional processing performed on the image data acquired by the transesophageal echocardiography probe.

Further, for example, in the embodiments described above, the example is explained in which the MPR images displayed on the display screen are still images; however possible embodiments are not limited to this example. For instance, the displayed MPR images may be moving images corresponding to one or more cardiac cycles.

Further, the constituent elements of the apparatuses illustrated in the drawings are based on functional concepts. Thus, it is not necessary to physically configure the constituent elements as indicated in the drawings. In other words, the specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

Further, with regard to the processes explained in the embodiments described above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and information including various types of data and parameters that are presented in the above text and the drawings.

Furthermore, the image processing method explained in any of the embodiments above may be realized by causing a computer such as a personal computer or a workstation to execute an image processing computer program prepared in advance. The image processing method may be distributed via a network such as the Internet. Further, the image processing method may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, so as to be executed as being read by a computer from the recording medium.

According to at least one aspect of the embodiments described above, it is possible to make simple and convenient the three-dimensional processing performed on the image data acquired by the transesophageal echocardiography probe.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising processing circuitry configured to:
   obtain volume video data of a patient acquired by a transesophageal echocardiography probe;
   set, with the volume video data, a three-dimensional coordinate system that matches a display orientation of image data of the patient acquired by a body-surface ultrasound probe, on a basis of a positional relationship between the transesophageal echocardiography probe and the patient;
   cause a display screen to display image data generated from the volume video data by using the set three-dimensional coordinate system;
   receive, from an operator, a designation related to calculating movement information in a region of interest of the patient, the designation being received in an image displayed on the display screen; and
   calculate the movement information by performing processing including a tracking process, while using the volume video data, wherein
   the processing circuitry obtains a rotation angle of the transesophageal echocardiography probe observed at a time of acquisition of pieces of volume data included in the volume video data, and
   the processing circuitry sets the three-dimensional coordinate system on basis of each rotation angle.

2. The ultrasound diagnosis apparatus according to claim 1, wherein the processing circuitry sets the three-dimensional coordinate system on the basis of the positional relationship between the transesophageal echocardiography probe and the patient in such a manner that, among three directions structuring the three-dimensional coordinate system of the volume video data, a first direction corresponding to an up-and-down direction of the display screen is inverted and that one selected from between a second direction and a third direction, which are other directions among the three directions besides the first direction, is also inverted.

3. The ultrasound diagnosis apparatus according to claim 1, wherein the processing circuitry switches between two types of three-dimensional mirror-image inverted coordinate systems that are possibly available with respect to the volume video data set with the three-dimensional coordinate systems, depending on whether or not each of the rotation angles is equal to or larger than a predetermined angle.

4. The ultrasound diagnosis apparatus according to claim 3, wherein
   the rotation angles are each defined so that a direction orthogonal to an extending direction of the transesophageal echocardiography probe is equal to 0 degrees, and
   the processing circuitry switches between the two types of three-dimensional mirror-image inverted coordinate systems, depending on whether or not each of the rotation angles is larger than either 90 degrees or −90 degrees.

5. The ultrasound diagnosis apparatus according to claim 1, wherein
   the processing circuitry detects a central axis of the region of interest and a reference cross-sectional plane passing through the central axis, from a piece of volume data corresponding to at least one temporal phase and being among pieces of volume data that correspond to a plurality of temporal phases and are included in the volume video data, and
   the processing circuitry sets the three-dimensional coordinate system on a basis of the central axis and the reference cross-sectional plane that were detected.

6. The ultrasound diagnosis apparatus according to claim 5, wherein the processing circuitry switches between two types of three-dimensional mirror-image inverted coordinate systems that are possibly available with respect to the volume video data set with the three-dimensional coordinate system, on a basis of the central axis and the reference cross-sectional plane.

7. The ultrasound diagnosis apparatus according to claim 1, wherein the processing circuitry adjusts an orientation of a display image generated from the volume video data in such a manner that a central axis of the region of interest corresponds to an up-and-down direction of the display screen.

8. The ultrasound diagnosis apparatus according to claim 1, wherein
the processing circuitry further obtains body-surface-derived volume video data of the patient acquired by the body-surface ultrasound probe,
when the body-surface-derived volume video data is obtained, the processing circuitry does not set the three-dimensional coordinate system with the body-surface-derived volume video data, and
when the volume video data is obtained, the processing circuitry sets the three-dimensional coordinate system with the volume video data.

9. The ultrasound diagnosis apparatus according to claim 1, wherein the region of interest is one selected from among a left ventricle, a right ventricle, a left atrium, and a right atrium of a heart of the patient.

10. An ultrasound diagnosis apparatus comprising processing circuitry configured to:
obtain volume data of a patient acquired by a transesophageal echocardiography probe and a rotation angle of the transesophageal echocardiography probe observed at a time of the acquisition of the volume data;
set, with the volume data, a three-dimensional coordinate system that matches a display orientation of image data of the patient acquired by a body-surface ultrasound probe, on a basis of the rotation angle of the transesophageal echocardiography probe; and
cause a display screen to display image data generated from the volume data by using the set three-dimensional coordinate system.

11. The ultrasound diagnosis apparatus according to claim 10, wherein the processing circuitry switches between two types of three-dimensional mirror-image inverted coordinate systems that are possibly available with respect to volume data set with the three-dimensional coordinate system obtained by inverting an up-and-down direction of the display screen, depending on whether or not the rotation angle is equal to or larger than a predetermined angle.

12. The ultrasound diagnosis apparatus according to claim 11, wherein
the rotation angle is defined so that a direction orthogonal to an extending direction of the transesophageal echocardiography probe is equal to 0 degrees, and
the processing circuitry switches between the two types of three-dimensional mirror-image inverted coordinate systems, depending on whether or not the rotation angle is larger than either 90 degrees or −90 degrees.

13. An image processing apparatus comprising processing circuitry configured to:
obtain volume video data of a patient acquired by a transesophageal echocardiography probe;
set, with the volume video data, a three-dimensional coordinate system that matches a display orientation of image data of the patient acquired by a body-surface ultrasound probe, on a basis of a positional relationship between the transesophageal echocardiography probe and the patient;
cause a display screen to display image data generated from the volume video data by using the set three-dimensional coordinate system;
receive, from an operator, a designation related to calculating movement information in a region of interest of the patient, the designation being received in an image displayed on the display screen; and
calculate the movement information by performing processing including a tracking process, while using the volume video data, wherein
the processing circuitry obtains a rotation angle of the transesophageal echocardiography probe observed at a time of acquisition of pieces of volume data included in the volume video data, and
the processing circuitry sets the three-dimensional coordinate system on basis of each rotation angle.

14. An image processing apparatus comprising processing circuitry configured to:
obtain volume data of a patient acquired by a transesophageal echocardiography probe and a rotation angle of the transesophageal echocardiography probe observed at a time of the acquisition of the volume data;
set, with the volume data, a three-dimensional coordinate system that matches a display orientation of image data of the patient acquired by a body-surface ultrasound probe, on a basis of the rotation angle of the transesophageal echocardiography probe; and
cause a display screen to display image data generated from the volume data by using the set three-dimensional coordinate system.

* * * * *